United States Patent
Szafron et al.

(10) Patent No.: US 12,193,689 B2
(45) Date of Patent: *Jan. 14, 2025

(54) SHAPE MEMORY EMBOLECTOMY DEVICES AND SYSTEMS

(71) Applicants: Lawrence Livermore National Security, LLC, Livermore, CA (US); The Texas A&M University System, College Station, TX (US)

(72) Inventors: Jason Szafron, Hamden, CT (US); Duncan Maitland, College Station, TX (US); Ward Small, IV, Livermore, CA (US); Patrick R. Buckley, Livermore, CA (US); Andrea D. Muschenborn, Bloomington, IN (US)

(73) Assignees: Lawrence Livermore National Security, LLC, Livermore, CA (US); The Texas A&M University System, College Station, TX (US)

( * ) Notice: Subject to any disclaimer, the term of this patent is extended or adjusted under 35 U.S.C. 154(b) by 78 days.

This patent is subject to a terminal disclaimer.

(21) Appl. No.: 17/881,684

(22) Filed: Aug. 5, 2022

(65) Prior Publication Data
US 2022/0370086 A1 Nov. 24, 2022

Related U.S. Application Data

(63) Continuation of application No. 16/701,417, filed on Dec. 3, 2019, now Pat. No. 11,406,401, which is a
(Continued)

(51) Int. Cl.
*A61B 17/22* (2006.01)
*A61B 17/00* (2006.01)
*A61B 17/221* (2006.01)

(52) U.S. Cl.
CPC .... *A61B 17/22* (2013.01); *A61B 2017/00526* (2013.01); *A61B 2017/00867* (2013.01);
(Continued)

(58) Field of Classification Search
CPC .................. A61B 17/22; A61B 17/221; A61B 2017/2212; A61B 2017/22094
See application file for complete search history.

(56) References Cited

U.S. PATENT DOCUMENTS 6,740,094 B2   5/2004   Maitland et al.
7,611,524 B1   11/2009  Maitland et al.
(Continued)

OTHER PUBLICATIONS

Singhal et al. "Ultra low density and highly crosslinked biocompatible shape memory polyurethane foams", Journal of Polymer Science Part B: Polymer Physics 50 (10), 2012, pp. 724-737.
(Continued)

*Primary Examiner* — Tuan V Nguyen
(74) *Attorney, Agent, or Firm* — Trop, Pruner & Hu, P.C.

(57) ABSTRACT

An embolectomy device comprised of an expansion unit and a support unit is disclosed. The expansion unit can be actuated in response to one or more external stimuli, and the support unit, located proximately to the expansion unit, provides a force to hold the expansion unit in place and to further induce the expansion unit's radial expansion. The radial expansion of the expansion unit causes the expansion unit to physically contact a blood clot, enabling the blood clot to be removed. In some embodiments, the expansion unit can be fabricated from a shape memory polymer foam. In some embodiments the support unit can be fabricated from any elastic material including, without limitation, shape memory alloys.

20 Claims, 11 Drawing Sheets

Related U.S. Application Data continuation of application No. 15/094,701, filed on Apr. 8, 2016, now Pat. No. 10,499,935.

(60) Provisional application No. 62/144,432, filed on Apr. 8, 2015.

(52) U.S. Cl.
CPC .............. *A61B 2017/00871* (2013.01); *A61B 2017/22094* (2013.01); *A61B 2017/2212* (2013.01)

(56) References Cited

U.S. PATENT DOCUMENTS

| | | | |
|---|---|---|---|
| 7,744,604 B2 | 6/2010 | Maitland et al. | |
| 8,900,265 B1 | 12/2014 | Ulm, III | |
| 9,039,733 B2 | 5/2015 | Wilson et al. | |
| 9,670,308 B2 | 6/2017 | Singhal et al. | |
| 2004/0199201 A1 | 10/2004 | Kellett et al. | |
| 2005/0228417 A1* | 10/2005 | Teitelbaum | A61B 17/22031 606/159 |
| 2008/0045881 A1 | 2/2008 | Teitelbaum et al. | |
| 2011/0125181 A1 | 5/2011 | Brady et al. | |
| 2013/0317541 A1 | 11/2013 | Singhal et al. | |
| 2013/0331689 A1 | 12/2013 | Le et al. | |
| 2014/0142207 A1 | 5/2014 | Singhal et al. | |
| 2015/0150672 A1 | 6/2015 | Ma | |
| 2015/0182209 A1 | 7/2015 | Cahill | |
| 2015/0305756 A1 | 10/2015 | Rosenbluth et al. | |

OTHER PUBLICATIONS

Szafron et al., "Design and Characterization of an Endovascular Mechanical Thrombectomy Device", Journal of Medical Devices, vol. 8, 2014, pp. 020910-1-020910-2.

* cited by examiner

SHAPE MEMORY EMBOLECTOMY DEVICES AND SYSTEMS

CROSS-REFERENCE TO RELATED APPLICATION

This application is a continuation of U.S. patent application Ser. No. 16/701,417, filed Dec. 3, 2019, which is a continuation of U.S. patent application Ser. No. 15/094,701, filed Apr. 8, 2016, now U.S. Pat. No. 10,499,935, issued Dec. 10, 2019 and entitled "Shape Memory Embolectomy Device And Systems", which claims priority to U.S. Provisional Patent Application No. 62/144,432 filed on Apr. 8, 2015 and entitled "Shape Memory Embolectomy Device." The content of each of the above applications is hereby incorporated by reference.

STATEMENT REGARDING FEDERALLY SPONSORED RESEARCH OR DEVELOPMENT

This disclosure was made with Federal Government support under Grant No. R01EB000462 awarded by the National Institute of Biomedical Imaging and Bioengineering. The Government has certain rights in the disclosure. Additionally, the United States Government has rights in this application pursuant to Contract No. DE-AC52-07NA27344 between the United States Department of Energy and Lawrence Livermore National Security, LLC for the operation of Lawrence Livermore National Laboratory.

TECHNICAL FIELD

The present disclosure provides an embolectomy device comprised of shape memory materials, exhibiting shape memory and mechanical properties optimized for removing blood clots from occluded blood vessels.

BACKGROUND

The presence of a blood clot blocking blood flow in the circulatory system causes thromboembolic vascular disease. Venous thromboembolisms affect more than 900,000 Americans each year, with 30% of those dying within 30 days and another 30% affected by recurring venous thromboembolisms within ten years.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION AND EXEMPLARY EMBODIMENTS

Figure 1:
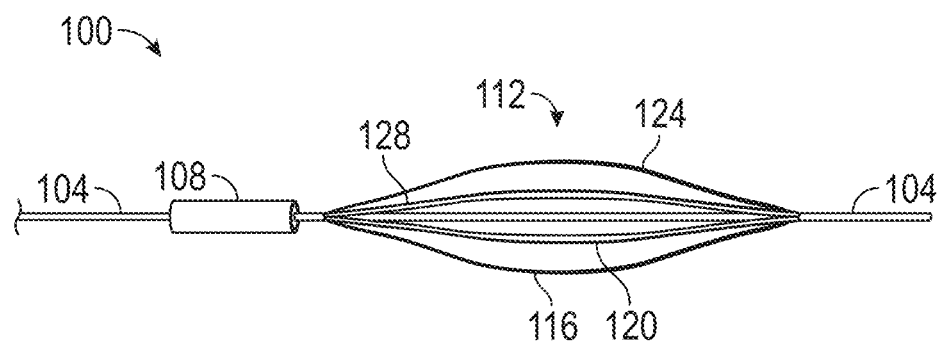
FIG. 1 depicts an example embolectomy device, configured to be inserted into a blood vessel with an occlusive blood clot in accordance with an embodiment of this disclosure.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s)

so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Applicant has determined conventional stent-like embolectomy devices fail to adequately mitigate distal embolization from blood clot fragmentation. Additionally, Applicant has determined the length of stent-like embolectomy devices reduces the maneuverability of these stent-like devices. These and other limitations necessitate a solution.

A disclosed embodiment is directed to an embolectomy device comprised of shape memory (SM) components. In one embodiment, an embolectomy device is comprised of a guidewire, at least one expansion unit, and at least one support unit. The expansion unit can be comprised of a shape memory polymer (SMP) foam in some embodiments. The support unit can be comprised of an elastic material, such as SM alloys and SMPs in some implementations. The support unit is configured to include struts that curve outward from the guidewire. The at least one support unit is affixed to the guidewire, and the at least one expansion unit is affixed to the guidewire proximate to the at least one support unit. The support unit provides structural support to the expansion unit. Additionally, the support unit can be fabricated in a geometry that collapses to a small radius after being forced into a small volume, such as the lumen of a catheter. Due to its elastic properties, the support unit can recover its larger radius geometry after entering a space with a larger volume. Actuation of the expansion unit causes the expansion unit to expand substantially in volume. In an embodiment, the expansion unit can be comprised of a SMP foam, which can be actuated through application to the SMP foam of any of heat, a solvent, laser irradiation, or resistive heating. Actuation refers to providing an external stimulus (e.g., exposure to warm blood or bodily fluids) to the expansion unit that induces the expansion unit to expand in volume. The support unit compresses against the expansion unit, holding the expansion unit in place and causing the expansion unit to expand outward radially, filling the occluded blood vessel and preventing a blood clot from slipping around the disclosed embolectomy device.

Another embodiment is directed to a method for removing blood clots using an embodiment of the embolectomy device. An embodiment of an embolectomy device can be advanced through a blood vessel and past a blood clot occluding the blood vessel. The expansion unit of the embolectomy device can be actuated to cause the volume of the expansion unit to increase substantially. Consequently, the expansion unit can physically contact the blood clot. The expanded size of the expansion unit can preclude the blood clot or pieces of the blood clot from escaping. The embolectomy device and catheter are retracted from the site of the blood clot, causing the blood clot to be dragged in the direction of the retraction. As the embolectomy device is dragged, the resulting force causes the support unit to press against the expansion unit, holding the expansion unit in place and inducing further radial expansion of the expansion unit. In one embodiment, the embolectomy device and catheter can be dragged to the location of a sheath, introduced into the blood vessel, and the sheath can be used to capture the blood clot. The sheath, containing the blood clot, can be removed.

A further embodiment of the disclosure is directed to a method for making an embodiment of the disclosed embolectomy device. A plurality of slits is cut into a segment of an elastic material to form a support unit containing struts. The support unit is heated. The support unit is cooled. The support unit is affixed to a guidewire. An expansion unit is excised from a homogeneous mass of SMP foam. The expansion unit is affixed to the guidewire proximate to the support unit.

As noted above, the description herein includes exemplary devices and methods that embody the present disclosure. However, it is understood that the described embodiments may be practiced without these specific details. For example, although FIG. 1 depicts an embodiment of an embolectomy device that includes a single expansion unit and a single support unit, other embodiments of the embolectomy device may include a plurality of expansion units and a plurality of support units. Additionally, although depictions of the support unit show a designated number of struts, fewer or more struts may be present in various embodiments of the support unit of the disclosed embolectomy device. Moreover, in some implementations, the at least one expansion unit can be epoxied onto the at least one support unit.

In an embodiment an embolectomy device can be comprised of a guidewire; at least one expansion unit; and at least one support unit, cut to contain a plurality of slits configured to form a flower-like structure comprised of a plurality of struts. The at least one support unit can be affixed to the guidewire. The at least one expansion unit can be affixed to the guidewire. The at least one expansion unit can be situated proximately to the support unit. The expansion unit can be comprised of a SMP foam. The support unit can be comprised of an elastic material such as a SM alloy or a SMP. Stainless steel and nitinol are non-limiting examples of SM alloys from which the support unit can be comprised.

In an embodiment, the embolectomy device can be appended to a catheter. The catheter, configured with the embolectomy device, can be advanced into a blood vessel containing a blood clot, and the embolectomy device can be advanced past a blood clot within the blood vessel. The expansion unit of the embolectomy device can be actuated to expand significantly in volume. In one embodiment, the expansion unit of the embolectomy device can be expanded by plasticization. For instance, water heated to approximately 37 degrees centigrade can induce the expansion unit of the embolectomy device to expand outward radially, thereby enlarging significantly in diameter. The term actuation refers to causing an expansion unit to transition from a crimped initial state to an expanded state by providing a stimulus to the expansion unit.

Hence, due to this outward radial expansion, the expansion unit of the embolectomy device can physically contact the blood clot. The expansion unit can contact the blood clot in a direction perpendicular to blood flow. The struts of the support unit of the embolectomy device can contact the expansion unit, holding the expansion unit in place. Thus, the expansion unit can capture the blood clot, holding the blood clot in place, and the support unit can hold the expansion unit in place, further compressing the expansion unit and further forcing it to expand outward radially. The embolectomy device and catheter can be retracted from the site of the blood clot, causing the blood clot to be dragged. In one embodiment, a sheath can separately be introduced into the blood vessel, and the blood clot can be dragged into the sheath. The sheath, with the blood clot located within it, can be removed. Due to the radial expansion of the expansion unit, which can capture the blood clot, and the deformation of the support unit, which can hold the expansion unit in place and which can induce further radial expansion of the expansion unit due to an axial force placed on the expansion unit, the embolectomy device needs only be advanced on the order of a centimeter or less outside the catheter to capture a blood clot.

FIG. 1 illustrates an example embodiment of the embolectomy device 100. The embolectomy device 100 includes a guidewire 104, an expansion unit 108, and a support unit 112. The support unit 112 can be affixed to the guidewire 104. The expansion unit 108 also can be affixed to the guidewire 104.

The expansion unit 108 may be comprised of any low density SMP foam in some embodiments. SMP foams exhibit an entropically driven SM effect. For example, the expansion unit 108 may be comprised from those SMP foams generally described in United States Patent Application Publication Number 20140142207 A1 entitled "Ultra Low Density Biodegradable Shape Memory Polymer Foams with Tunable Physical Properties." In one embodiment, an expansion unit can be crimped to 20% of its initial diameter and can retain its ability to recover its initial geometry, thereby providing a mechanism advance such an expansion unit through a catheter. However, in other embodiments different low density SMP foams can be used to constitute the expansion unit 108. For example, a SMP foam described in United States Patent Application Publication 20140142207A1 could be chemically modified to bind to blood clots. The SMP unit 108 can be fabricated from the chemically modified SMP foam. Although depicted as cylinder, the expansion unit 108 can be fashioned into any geometry optimized to capture a blood clot. For instance, the expansion unit 108 can be fashioned into a sphere, a cone, or a barrel in some embodiments. SMP foams can expand in volume by as much as seventy times their original volumes. In an embodiment, an expansion unit can be comprised of a SMP foam with a low glass transition temperature Tg; hence, exposure to blood can cause these expansion units to actuate.

The support unit 112 may include a plurality of struts 116, 120, 124, and 128 that expand outward from the guidewire 104. The length of the plurality of struts 116, 120, 124, and 128 can vary, thereby affecting the dimensions of the support unit 112. The support unit 112 can be fabricated from any elastic material that exhibits a pseudoelastic effect. For example, the support unit 112 can be fabricated from any of nitinol, stainless steel, platinum, a platinum alloy, or other elastic metal alloy. The support unit 112 also can be fabricated from a SMP. In one embodiment, the support unit 112 can be fabricated from a segment of nitinol tubing. Nitinol can recover from strains of up to eight percent. An excimer laser can be used to cut a plurality of slits lengthwise in the nitinol tubing. These slits can form struts that fashion the nitinol tubing into a flower-like structure, wherein each strut constitutes a "petal" of the flower-like structure as depicted in FIG. 1. As the embolectomy device is moved through a blood vessel, the support unit 112 can deform, pushing against the expansion unit 108, holding the expansion unit 108 in place and causing the expansion unit 108 to further expand outward radially, thereby increasing the surface area contact between the expansion unit 108 and a blood clot.

Since the support unit 112 can be set through mechanical constraint and heat treatment, the support unit 112 can be fabricated in a geometry that collapses to a small radius after being forced into the lumen of a catheter or other delivery device. Pushing the support unit 112 outside a catheter or other shape constrained delivery device can permit the support unit 112 to recover the larger radius geometry of the support unit 112. The guidewire 104 can be fabricated from any of nitinol, stainless steel, or a platinum alloy. The guidewire 104 also can be fabricated from other materials that can withstand high strains. In some embodiments, the guidewire 104 may be replaced with another suitable substrate capable of withstanding strain while providing a support for the support unit 112 and the expansion unit 108.

Figure 2A:
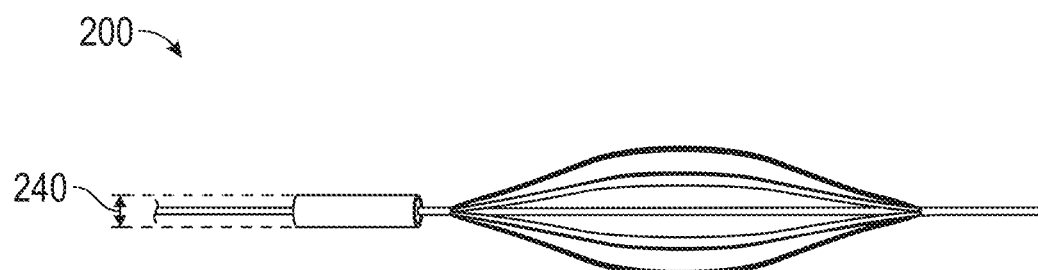
FIG. 2A depicts an example embolectomy device in a non-actuated configuration in accordance with an embodiment of this disclosure.
Figure 2B:
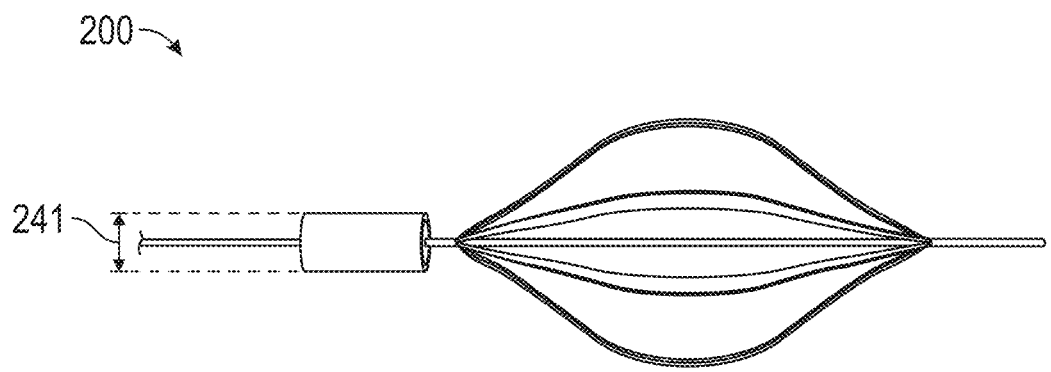
FIG. 2B depicts an example embolectomy device in an actuated configuration in accordance with an embodiment of this disclosure.

FIG. 2A illustrates the disclosed embolectomy device 200 in a crimped, non-actuated state. FIG. 2B depicts the disclosed embolectomy device 200 in an actuated state. In embodiments in which the expansion unit 108 of the embolectomy device 200 is fabricated from SMP foams, the expansion unit 108 can be actuated by exposure of the expansion unit 108 to water at a temperature range of between 20 degrees centigrade and 100 degrees centigrade. Similarly, when deployed in the body, heat from blood can be used to induce actuation of the expansion unit 108 in some embodiments. In other implementations, any of a solvent, laser irradiation, or resistive heating can be employed to actuate the expansion unit 108 in embodiments in which the expansion unit 108 is formed from SMP foams.

Figure 3A:
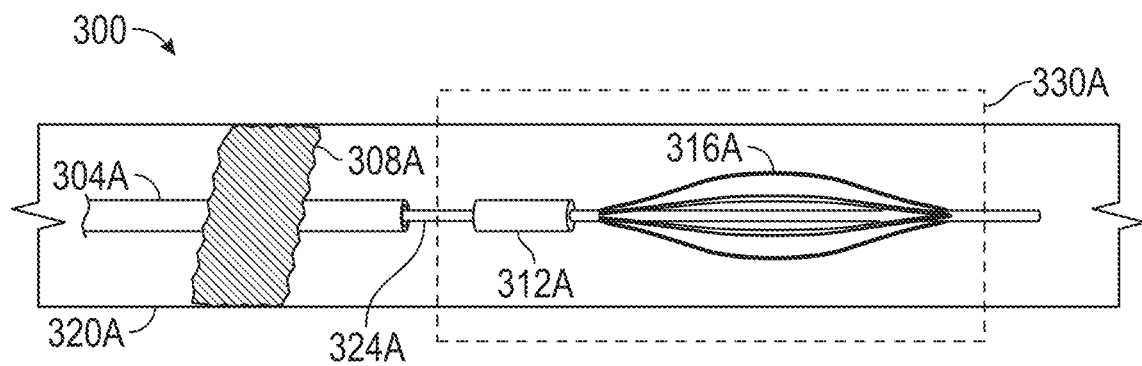
FIG. 3A depicts the deployment of an example embolectomy device within a blood vessel with an occlusive blood clot in accordance with an embodiment of this disclosure.
Figure 3B:
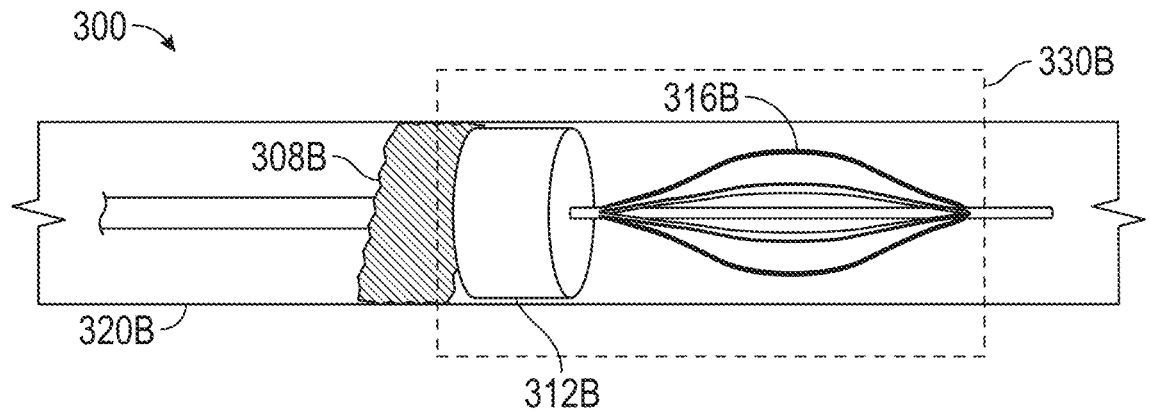
FIG. 3B depicts actuation of the example embolectomy device to remove an occlusive blood clot in accordance with an embodiment of this disclosure.
Figure 3C:
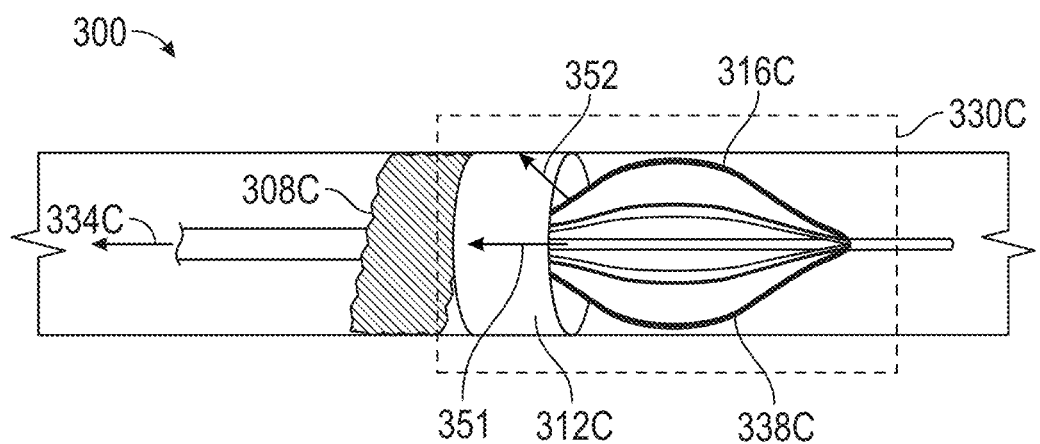
FIG. 3C depicts removal of a blood clot from a blood vessel using the example embolectomy device in accordance with an embodiment of this disclosure.

FIGS. 3A, 3B, and 3C depict use of an embolectomy device 330A, 330B, 330C to remove a blood clot 308A, 308B, 308C from a blood vessel 320A, 320B, 320C. FIG. 3A illustrates a blood vessel 320A occluded with a blood clot 308A. In an embodiment, an embolectomy device 330A comprised of a guidewire 324A, an expansion unit 312A, and a support unit 316A can be affixed to a catheter 304A. As illustrated in FIG. 3A, the embolectomy device 330A is in a non-actuated state. The embolectomy device 330A in a non-actuated state can be guided past the blood clot 308A. The embolectomy device 330A can be actuated. In one embodiment, water heated to between 20 degrees centigrade and 100 degrees centigrade can be delivered through the catheter to contact the expansion unit 312A, 312B, 312C. Heat from contact with the water can induce the expansion unit 312A, 312B, 312C to actuate, thereby leading to a significant expansion of the volume of the expansion unit 312A, 312B, 312C as depicted in FIG. 3B in embodiments in which the expansion unit 312A, 312B, 312C is fabricated from a SMP foam. As shown in FIG. 3B, the expansion unit 312B is in physical contact with the blood clot 308B, immobilizing the blood clot. The support unit 316B provides support to the expansion unit 312B, holding the expansion unit 312B in place. Additionally, the support unit 316B can exert an axial force on the expansion unit 312B causing the expansion unit 312B to further expand outward radially, thereby increasing the surface area contact between the expansion unit 312B and the blood clot 308B. Therefore, the expansion unit 312B holds the blood clot 308B in place, and the support unit 316 holds the expansion unit 312B in place. As illustrated in FIG. 3C, a force 334C can be applied to extract the blood clot 308C. As the embolectomy device 330C is pulled in the direction of the force 334C, the expansion unit 312C can push against the blood clot 308C. The force 334C can cause the struts 338C of the support unit 316C to deform, thereby exerting a force against the expansion unit 312C.

Figure 4A:
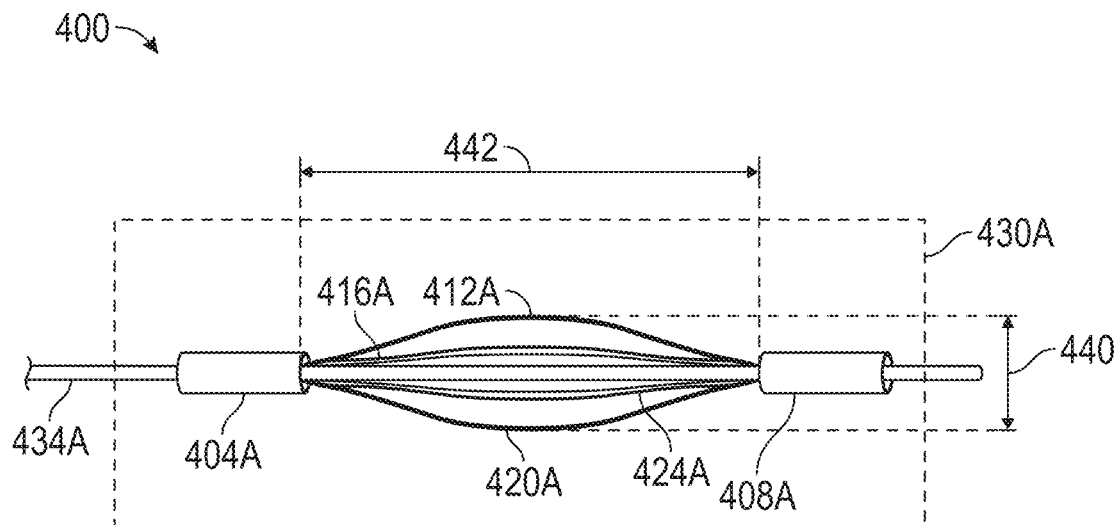
FIG. 4A depicts an example of a support unit of an embolectomy device in a relaxed state in accordance with an embodiment of this disclosure.
Figure 4B:
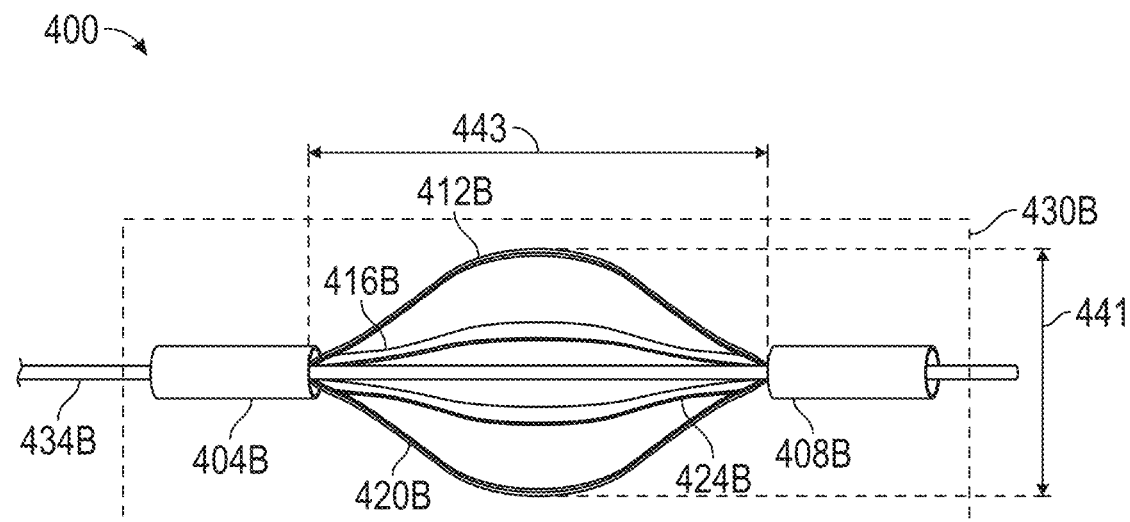
FIG. 4B depicts an example of a support unit of an embolectomy device in a deformed state in accordance with an embodiment of this disclosure.

FIGS. 4A and 4B depict the support unit 430A, 430B in a relaxed state and a deformed state, respectively. In an embodiment, the support unit 430A, 430B can be fashioned from nitinol. For example, an excimer laser can be used to cut a plurality of slits into a segment of nitinol tubing. In one embodiment, four such slits can be created, but in other embodiments fewer or more slits can be fashioned. The slits can be configured to form the struts 412A, 412B, 416A, 416B, 420A, 420B, 424A, 424B shown in FIGS. 4A and 4B, permitting the support unit 430A, 430B to be configured in the geometry shown in FIGS. 4A and 4B. Hence, the nitinol tubing, containing the struts, can be placed into an aluminum fixture to compress the nitinol tubing into a flower-like geometry, as shown, for example, in FIGS. 4A and 4B. Larger diameter nitinol tubing can form collars 404A, 408A, 404B, 408B to constrain and direct the compression of the nitinol to a configuration that serves to reduce stress on the more fragile sections of the support unit 430A, 430B. In one embodiment, the support unit 430A, 430B can be affixed to a nitinol guidewire 434A, 434B by using a 1064 nm YAG laser welder. Other techniques can be used to affix the support unit 430A, 430B to the guidewire 434A, 434B. As illustrated in FIG. 4B, the struts 412A, 412B, 416A, 416B, 420A, 420B, and 424A, 424B can expand outward from the guidewire 434A, 434B.

Figure 5:
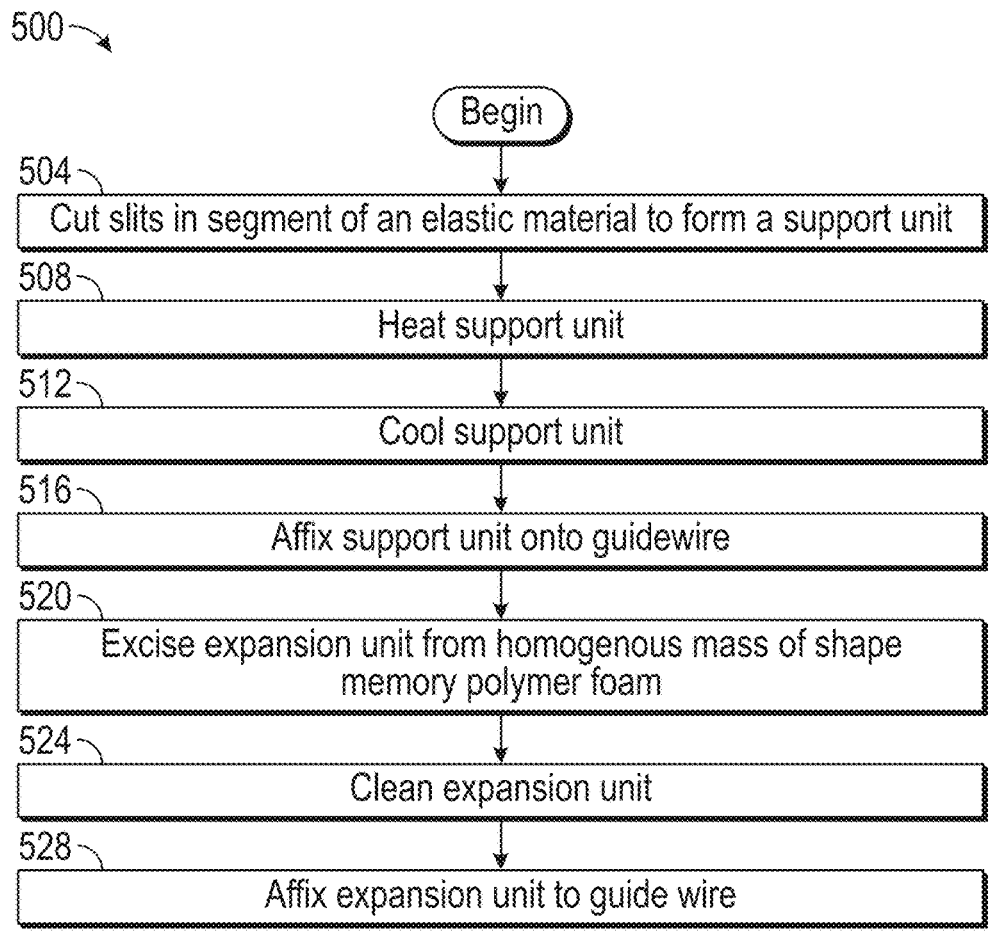
FIG. 5 is a flow diagram illustrating example operations to fabricate an embodiment of the disclosed embolectomy device in accordance with an embodiment of this disclosure.

FIG. 5 is a flow chart 500 that depicts example operations to fabricate the disclosed embolectomy device. At 504 slits are cut into a segment of an elastic material to form a support unit. At 508, the support unit can be heated. For instance, a furnace can be used to heat the support unit. At 512, the support unit can be cooled. For example, room temperature water can be used to quench the support unit. At 516, the support unit can be affixed onto a guidewire. In one embodiment, the support unit can be welded onto the guidewire. For instance, a laser welder can be used to affix the support unit onto the guidewire. At 520, an expansion unit can be excised from a homogeneous mass of SMP foam. In one embodiment, the expansion unit can be in the form of a cylinder. In other embodiments, the expansion unit can be fashioned into different shapes. For example, in an embodiment, a cylinder of SMP foam that is approximately 1.5 times the diameter of a blood vessel to be treated can be fashioned into an expansion unit. At 524, the expansion unit is cleaned and etched. For example, chemical washes can be used to clean and etch the expansion unit. At 528, the expansion unit is affixed onto the guidewire proximate to the support unit. In one embodiment, the expansion unit can be crimped onto the guidewire using a stent crimper, thereby drastically reducing the diameter of the expansion unit. The expansion unit can be fabricated from SM foams described in Singhal, P., Rodriguez, J. N., Small, W., Eagleston, S., Van de Water, J., Maitland, D. J., and Wilson, T. S., 2012, "Ultra low density and highly crosslinked biocompatible shape memory polyurethane foams," Journal of Polymer Science Part B: Polymer Physics 50 (10), pp. 724-737.

Figure 6:
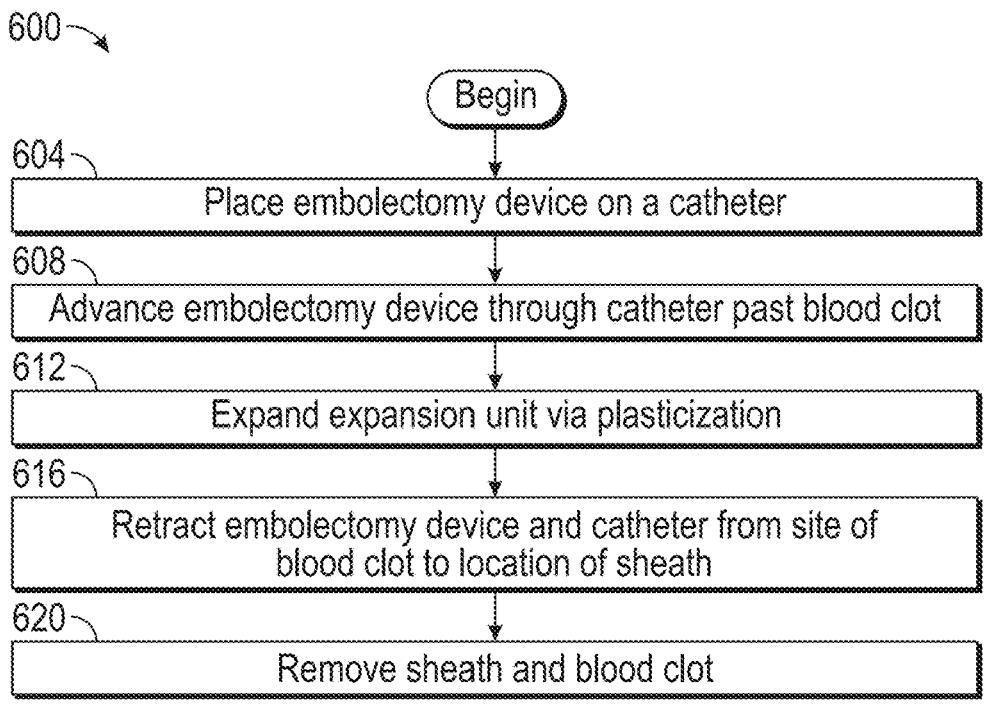
FIG. 6 is a flow diagram illustrating example operations to use an embodiment of the disclosed embolectomy device to remove an occlusive blood clot from a blood vessel in accordance with an embodiment of this disclosure.

FIG. 6 is a flow chart 600 that depicts example operations for use of the disclosed embolectomy device to remove a blood clot from an occluded blood vessel. At 604, the embolectomy device is placed on a catheter. At 608, the disclosed embolectomy device is advanced through the catheter and past the blood clot. At 612, the expansion unit is actuated, causing it to increase substantially in volume. In one embodiment, water at a temerate between 20 degrees centigrade and 100 degrees centigrade can be used to actuate the expansion unit in embodiments in which the expansion unit is comprised of SMP foams. In other embodiments, solvents can be used to actuate the expansion unit in implementations in which the expansion unit is comprised of SMP foams. As the expansion unit expands in volume, the expansion unit contacts the blood clot. Meanwhile, the support unit remains in contact with the expansion unit, pressing against the expansion unit and causing the expansion unit to further contract and expand outward radially. At 616, the disclosed embolectomy device and catheter is retracted from the site of the blood clot. As the embolectomy device is directed away from the site of the blood clot, the embolectomy device drags the blood clot along. In an embodiment, a sheath can be inserted near the site of the blood clot, and the blood clot can be dragged into the sheath. At 620, the sheath and blood clot can be removed.

Figure 7:
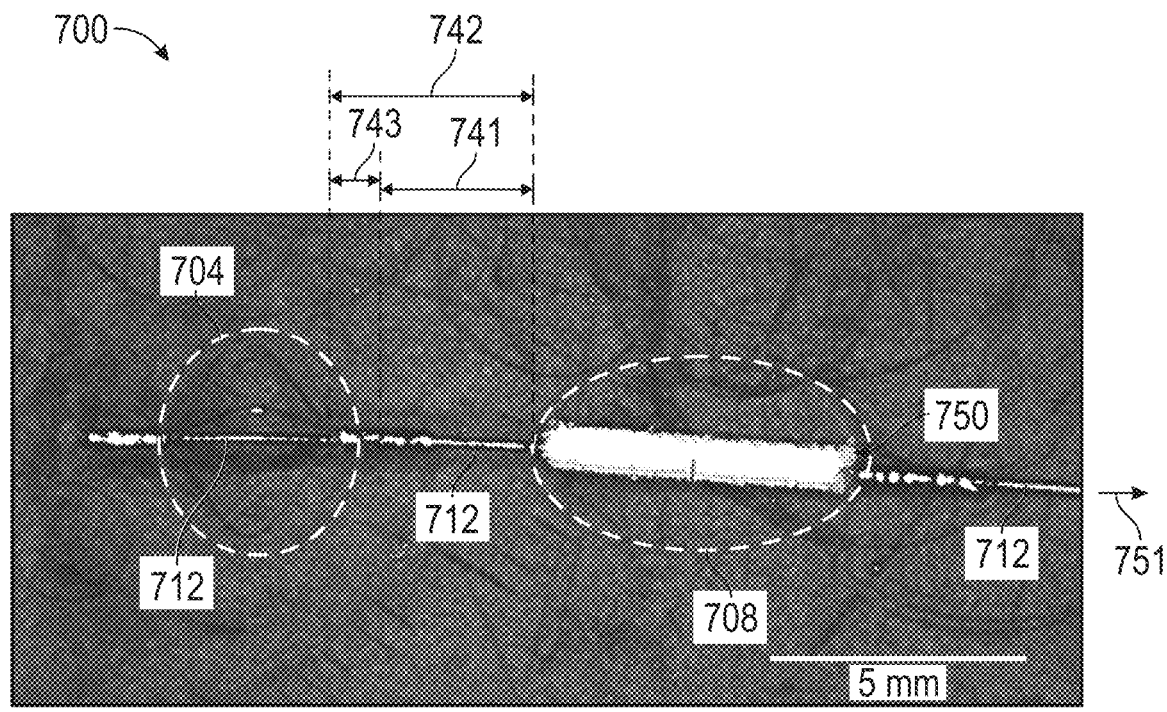
FIG. 7 is an experimental example of a disclosed embolectomy device in accordance with an embodiment of this disclosure.
Figure 8:
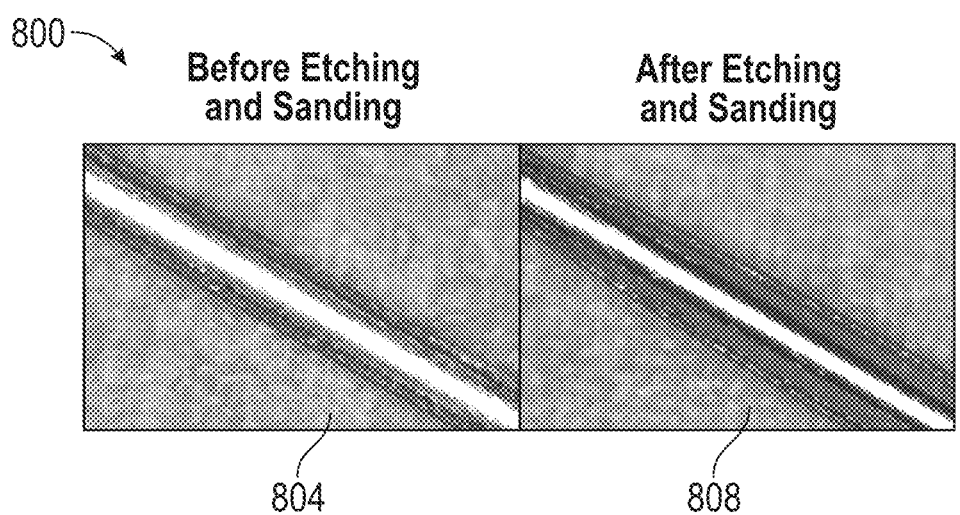
FIG. 8 depicts experimental examples of the support unit of the disclosed embolectomy device in accordance with an embodiment of the disclosure.

FIG. 7 depicts an example embodiment of the disclosed embolectomy device 700. The support unit 704 was fabricated from nitinol. In particular, a piece of nitinol tubing was cut using an excimer laser cutter (RapidX, Resonetics). The shape of the cut nitinol tubing consisted of a 7 mm section of 0.016" OD and 0.013" ID tubing cut with 4, 5 mm long axial slits with a 1 mm gap on each of the edges of the slits. The slits were spaced equally around the radius of the nitinol tubing. The cut nitinol tubing with slits was placed over a 0.010" diameter nitinol wire and rolled on 600 grit sandpaper for 30 seconds to remove burs created by laser cutting. The cut nitinol tubing was etched using 5 M potassium hydroxide (KOH) for 30 minutes at 120° C. while being stirred with a magnetic stirring bar. The cut nitinol tubing also was placed in a sonicator (3510, Branson) with a 100% isopropyl alcohol solution for one minute to remove any soluble dirt particles from the surface of the cut nitinol tubing. FIG. 8 is an image of the cut nitinol tubing 800. The cut nitinol tubing 800 is depicted before etching and sanding 804 and after etching and sanding 808. The cut, sanded, and etched nitinol tubing 808 was placed into an aluminum fixture to compress the nitinol tubing into a flower-like geometry.

Figure 9A:
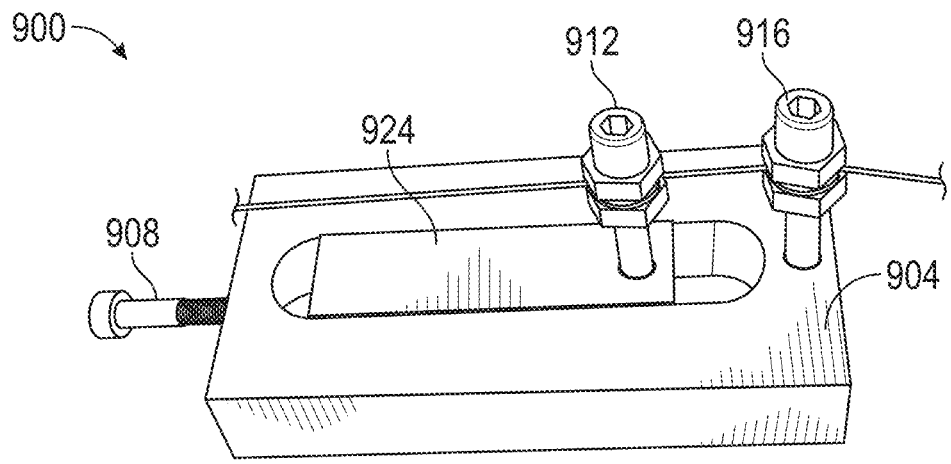
FIGS. 9A, 9B, and 9C depict an example set-up to produce an embodiment of a support unit according to an embodiment of the disclosure.
Figure 9B:
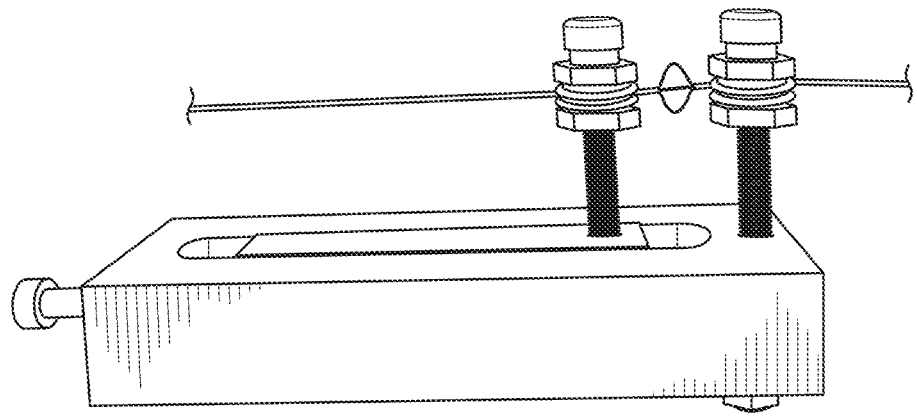
Figure 9C:
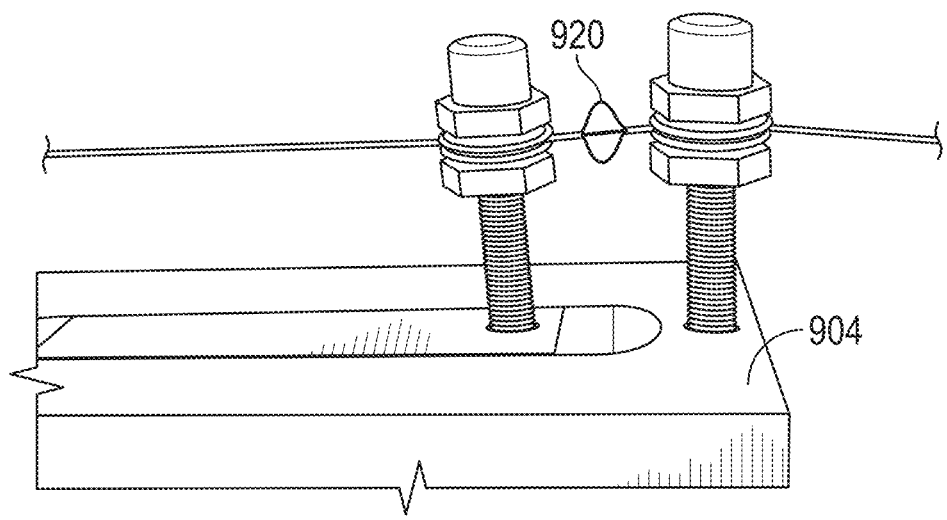

FIG. 9 depicts the aluminum fixture 900 used to form the support unit 704. The aluminum fixture 900 was fabricated from a sliding aluminum wedge placed within a hollowed-out channel in an aluminum block 904. A screw 908 was placed into a threaded hole on one of the ends of the aluminum block 904 to provide force to move the block down the channel. Screws 912, 916 also were placed upright in the sliding portion 924 and the aluminum block 904 in threaded holes. A hole was bored through the shank of each upright screw at the same height. To set the shape of the nitinol tubing, a wire was placed through the center of the nitinol tubing, which was subsequently placed through the holes on the two upright screws in the aluminum fixture 900. Washers were secured around the wire to hold it in place. By inserting the screw used to push the sliding component 924, the nitinol tubing was compressed between the two sets of washers on each screw, which served to constrain the nitinol tubing into a compressed secondary geometry 920. Heating in a furnace at 550 degrees C., followed by quenching in room temperature water, set the unstrained shape to match the compressed secondary geometry 920.

In some embodiments of the procedure employed to fabricate the support unit 704, the amount of axial compression was varied to affect the failure force during tensile testing. In some embodiments, the support unit 704 was compressed from an axial length of 7 mm to 6.25 mm, but in other implementations, the SM ally unit 704 was compressed from 7 mm to 5.75 mm of axial length.

Figure 10:
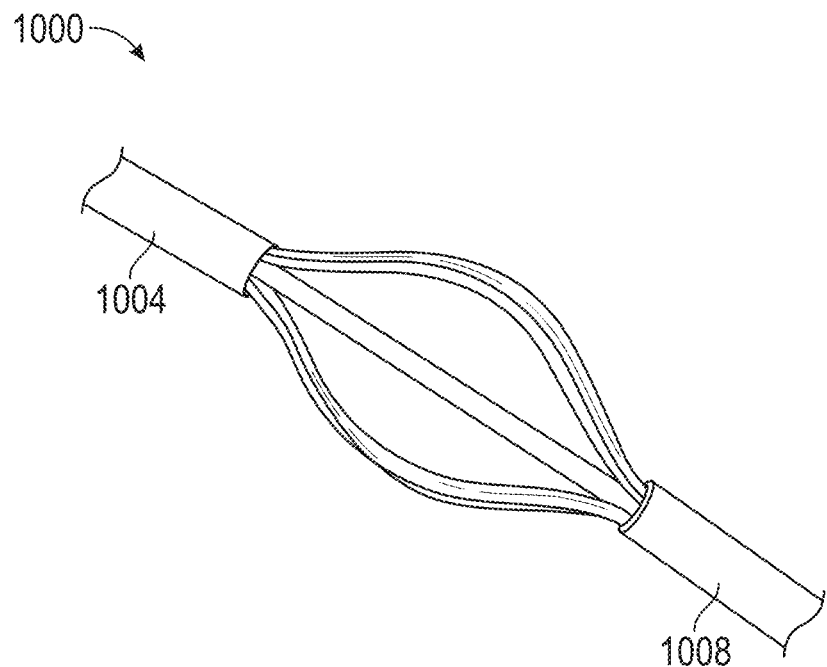
FIG. 10 depicts an alternative embodiment of a support unit according to an embodiment of the disclosure.

FIG. 10 illustrates an alternative implementation of a support unit 1000. As depicted in FIG. 10, sections of larger diameter nitinol tubing, referred to as collars 1004, 1008, were used during the shape setting process to constrain and direct the compression of the nitinol to a configuration that served to reduce stress on the more fragile sections of the support unit 1000. The collars 1004, 1008 placed around the nitinol tubing were typically 1.5 mm in length and 0.023" OD and 0.020" ID.

Figure 11A:
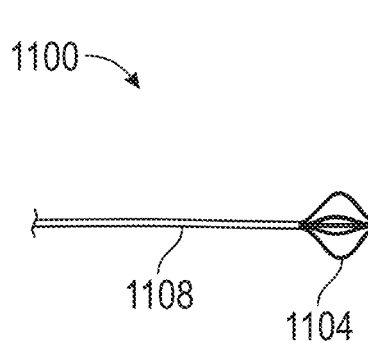
FIGS. 11A and 11B depict an implementation of a support unit in a relaxed and deformed state, respectively, according to an embodiment of the disclosure.
Figure 11B:
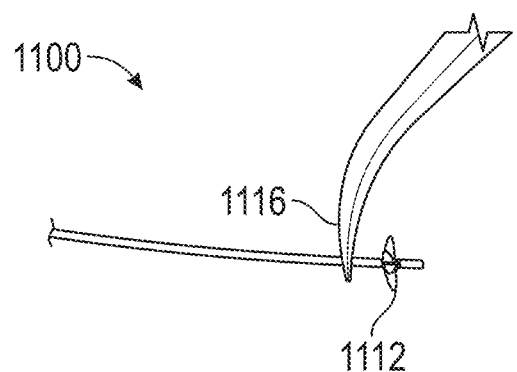

As shown in FIG. 11, an embodiment of the support unit 1104 was affixed to a guidewire 1108. In an implementation, the support unit 1104 was affixed to a 5' segment of 0.010" nitinol guidewire 1108 using a 1064 nm YAG laser welder (i990, LaserStar). In this embodiment, the support unit 1104 was welded at the distal tip of the guidewire 1108 to allow for compression 1112 of the support unit 1104 when a force 1116 was applied to the proximal end of the support unit 1104.

To fabricate the expansion unit, a cylinder of SMP foam oversized to approximately 1.5 times the diameter of the blood vessel to be treated was excised from a block of SMP foam. The targeted blood vessel to be treated was 4 mm in diameter; therefore, a 6 mm diameter sample of SMP foam was used. A 6 mm biopsy punch was used to remove the SMP foam sample from a large block of SMP foam. A razor blade was used to cut the sample of SMP foam to an axial length of 5 mm. The SMP foam sample was put into a stent crimper (SC250, Machine Solutions), where the diameter of the SMP foam sample was drastically reduced to a new crimped geometry after being heated to 100 degrees C. The SMP foam sample was cooled to room temperature over the course of two hours to set the secondary geometry of the SMP foam sample. The SMP foam sample was transferred from the crimping wire to a nitinol guidewire. The crimped diameter of the resulting expansion unit was approximately 1 mm.

In one embodiment, the expansion unit was epoxied to the support unit. UV curable, medical grade epoxy was spread around a proximal collar of a support unit using a cotton swab. The expansion unit was placed around the epoxied portion and was secured to the support unit though attachment to the collar. The UV epoxy was cured using a UV light (Series 1000, OmniCure).

In an implementation, a pusher portion of nitinol tubing was placed proximal to the expansion unit. In such an embodiment, the pusher can be included to provide pushing force on the surface of the expansion unit to prevent it from sliding along the guidewire as the embolectomy device is advanced towards a blood clot. In this particular embodiment, the pusher was constructed by welding a 2.5 mm piece of 0.016" OD and 0.013" ID nitinol tubing around the guidewire of the embolectomy device. Then a larger diameter, similar length piece of tubing made from 0.023" OD and 0.020" ID nitinol was welded around the smaller piece of tubing to ensure that the pusher could provide enough surface area to produce adequate force to move the expanding expansion unit along the catheter. The distal end of the pusher was located ~13 mm from the tip of the guidewire to allow for the support unit to be compressed radially and expanded axially when placed in a catheter without interfering with the pusher or expansion unit.

Figure 12:
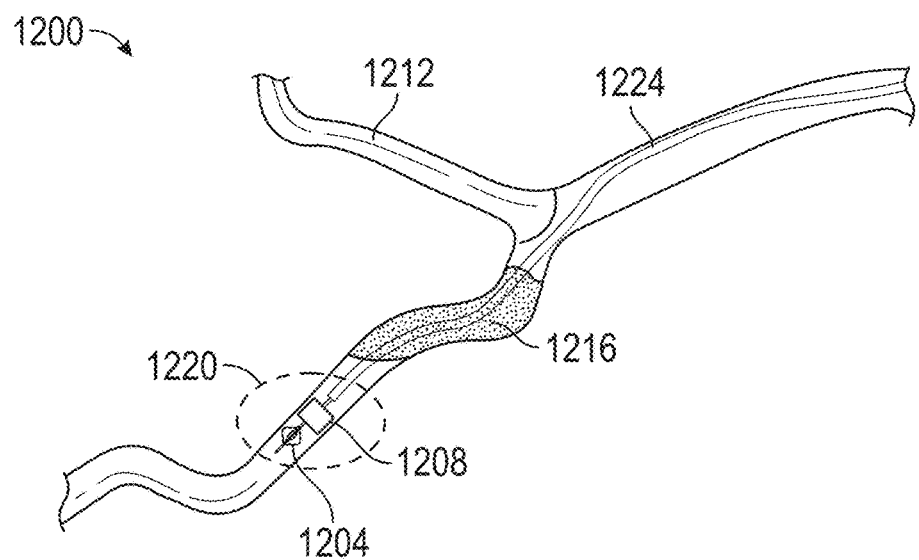
FIG. 12 depicts an embodiment of the disclosed embolectomy device deployed in an experimental setup of a blood vessel according to an embodiment of the disclosure.

FIG. 12 depicts an experimental setup 1200 involving an embodiment of the disclosed embolectomy device 1220. The embodiment of the embolectomy device 1220 included a support unit 1204 and an expansion unit 1208. As depicted in FIG. 12, the expansion unit 1208 has been actuated. In the depicted implementation, the embolectomy device 1220 was delivered to the site of a blood clot 1216 via a catheter 1224. In particular and as part of the experiment, a 5F catheter 1224 was deployed through a Luer lock, and the tip of the catheter 1224 was placed distal to the blood clot 1216. The catheter 1224 was flushed with body temperature water in an attempt to remove bubbles from the experimental setup 1200. The embolectomy device 1220 was fed through the lumen of the catheter 1224 and advanced out of the catheter 1224 to permit expansion of the expansion unit 1208. In one implementation of the experimental setup 1200, a syringe filled with body temperature water was injected through the catheter 1224 around an embodiment of the embolectomy device 1220 to induce actuation of the expansion unit of the embolectomy device 1220. In the experimental setup 1200, once the embolectomy device 1220 was deployed, the catheter 1224 was retracted proximal to the blood clot 1216, and the embolectomy device 1220 was used to extract the blood clot 1216.

Figure 13:
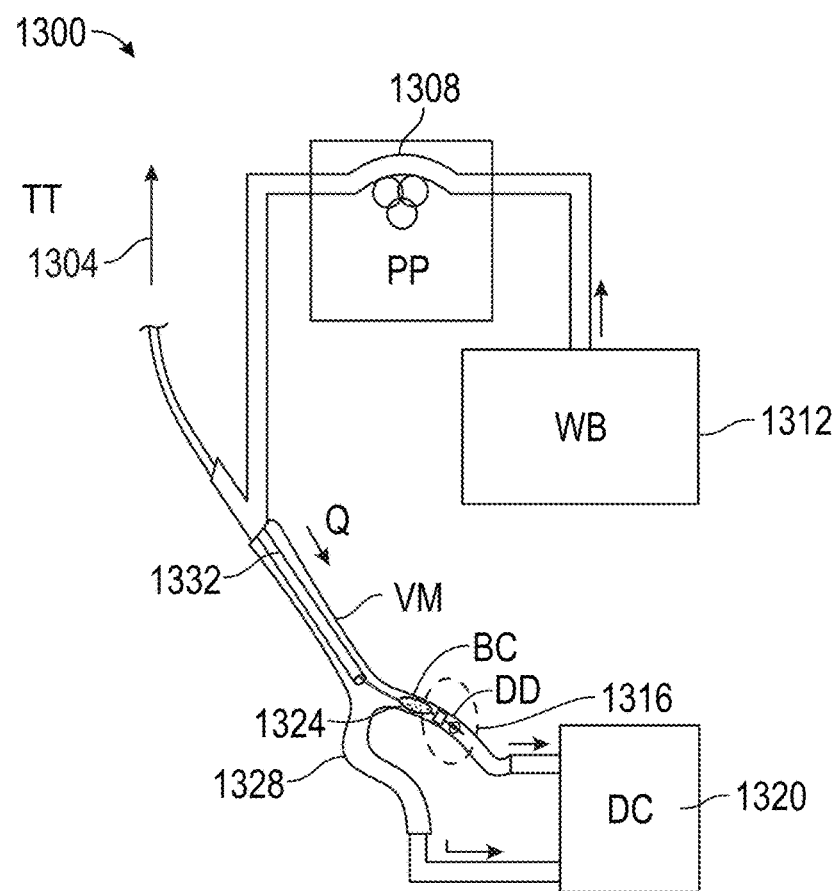
FIG. 13 depicts an embodiment of the disclosed embolectomy device deployed in an experimental setup equipped with a device capable of measuring tensile forces according to an embodiment of the disclosure.
Figure 14A:
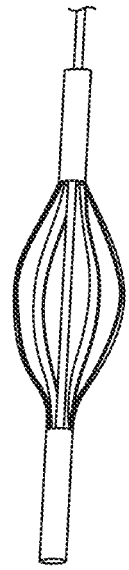
FIGS. 14A and 14B depict certain experimental results derived from tensile testing of certain embodiments of the embolectomy device according to embodiments of the disclosure.
Figure 14A:
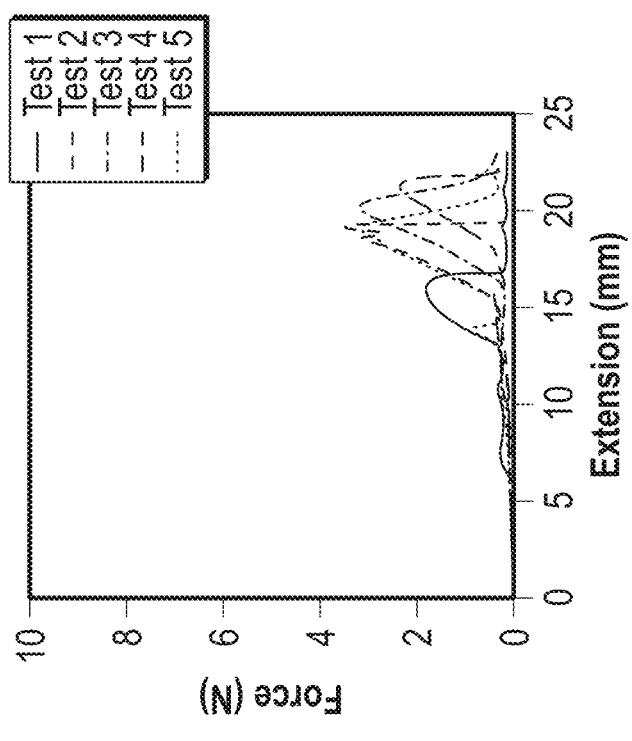
Figure 14A:
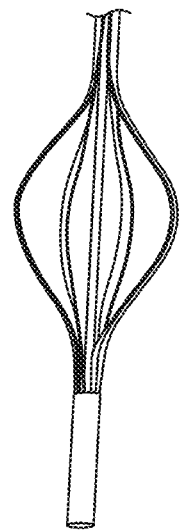
Figure 14A:
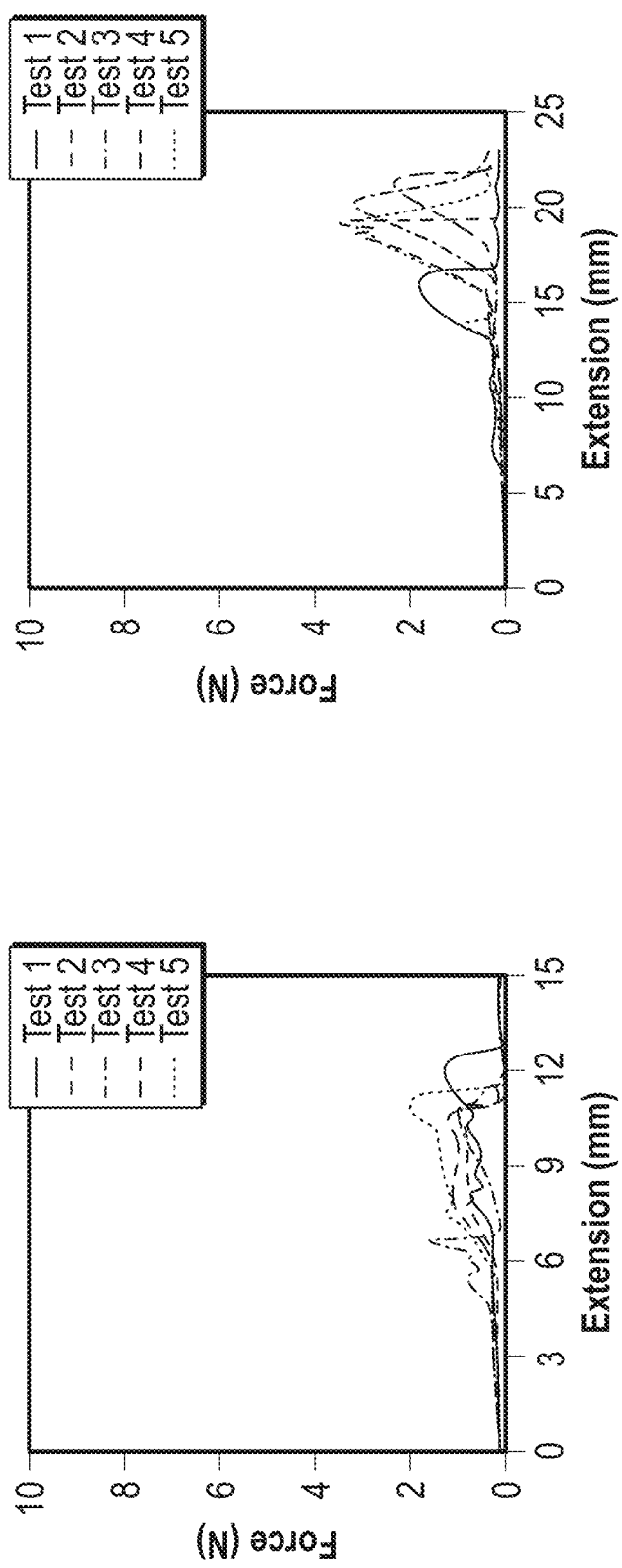
Figure 14B:
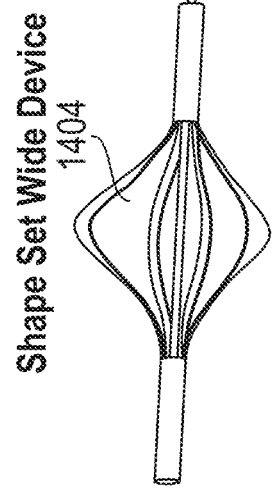
Figure 14B:
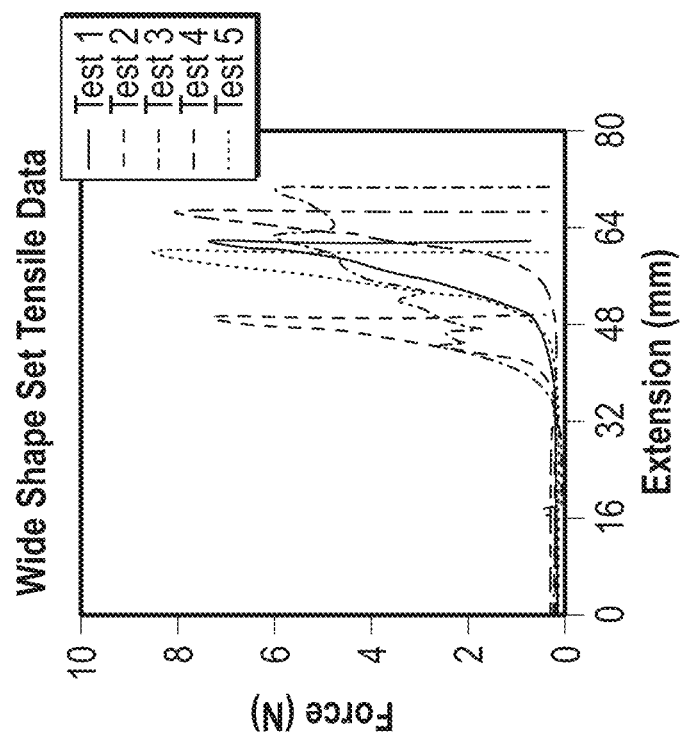
Figure 14B:
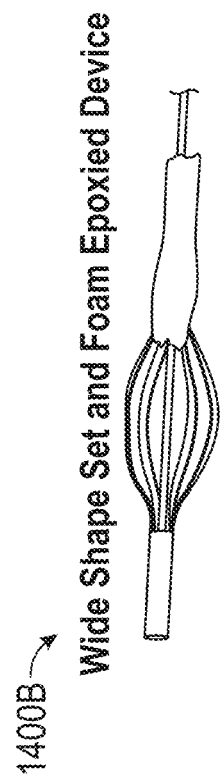
Figure 14B:
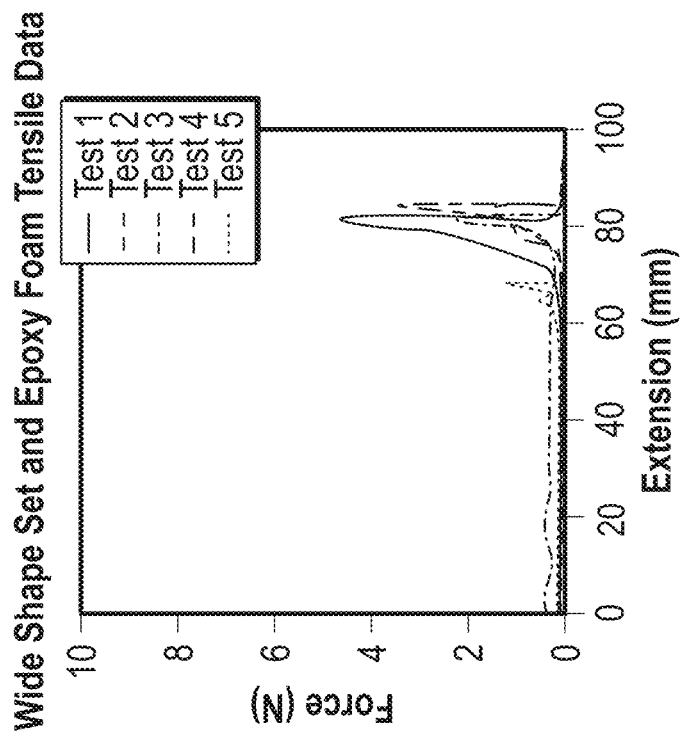

Retraction force studies were performed in connection with the experimental setup 1200. The experimental setup 1200 was modified as depicted in FIG. 13 to measure tensile forces to which an embodiment of the embolectomy device 1220 was subjected. The modified experimental setup 1300 includes a blood vessel model 1328, a catheter 1332, an embodiment of the embolectomy device 1316, a tensile tester 1304, a peristaltic pump 1308, a water bath 1312, and a discharge container 1320. An embodiment of the embolectomy device 1316 was affixed to the tensile tester (MTS, Synergie, 50 N load cell as an example) 1304 through a clamp around the proximal tip of the guidewire of an embodiment of the embolectomy device 1316. The remainder of the guidewire of an embodiment of the embolectomy device 1316 went through a conduit to align the embodiment of the embolectomy device 1316. The end of the alignment conduit acted as a stopper by providing a hole that was sufficiently large to pass the guidewire and support unit of the embodiment of the embolectomy device 1316 but too small to pass the expansion unit of the embodiment of the embolectomy device 1316. Force caused by the tensile tester 1304 pulling on the guidewire compressed the expansion unit and the support unit of the embodiment of the embolectomy device 1316 against the stopper until the embodiment of the embolectomy device 1316 failed. Failure was evidenced by a sharp drop off in force being recorded by the tensile tester 1304. Retraction force was measured as the tensile tester 1304 pulled an embodiment of the embolectomy device 1316 and blood clot 1324 through the mock-up blood vessel 1328 at a rate of 75 mm/minute.

Various experimental embodiments of the embolectomy device were tested using the experimental setup described in FIG. 13. FIG. 14 illustrates experimental results along with images of the support unit of each tested implementation of the embolectomy device. In one experiment, an embodiment of the embolectomy device, the support unit 1404 of which is depicted in FIG. 14, withstood forces of, on average, 7.43±0.94 N.

Figure 15:
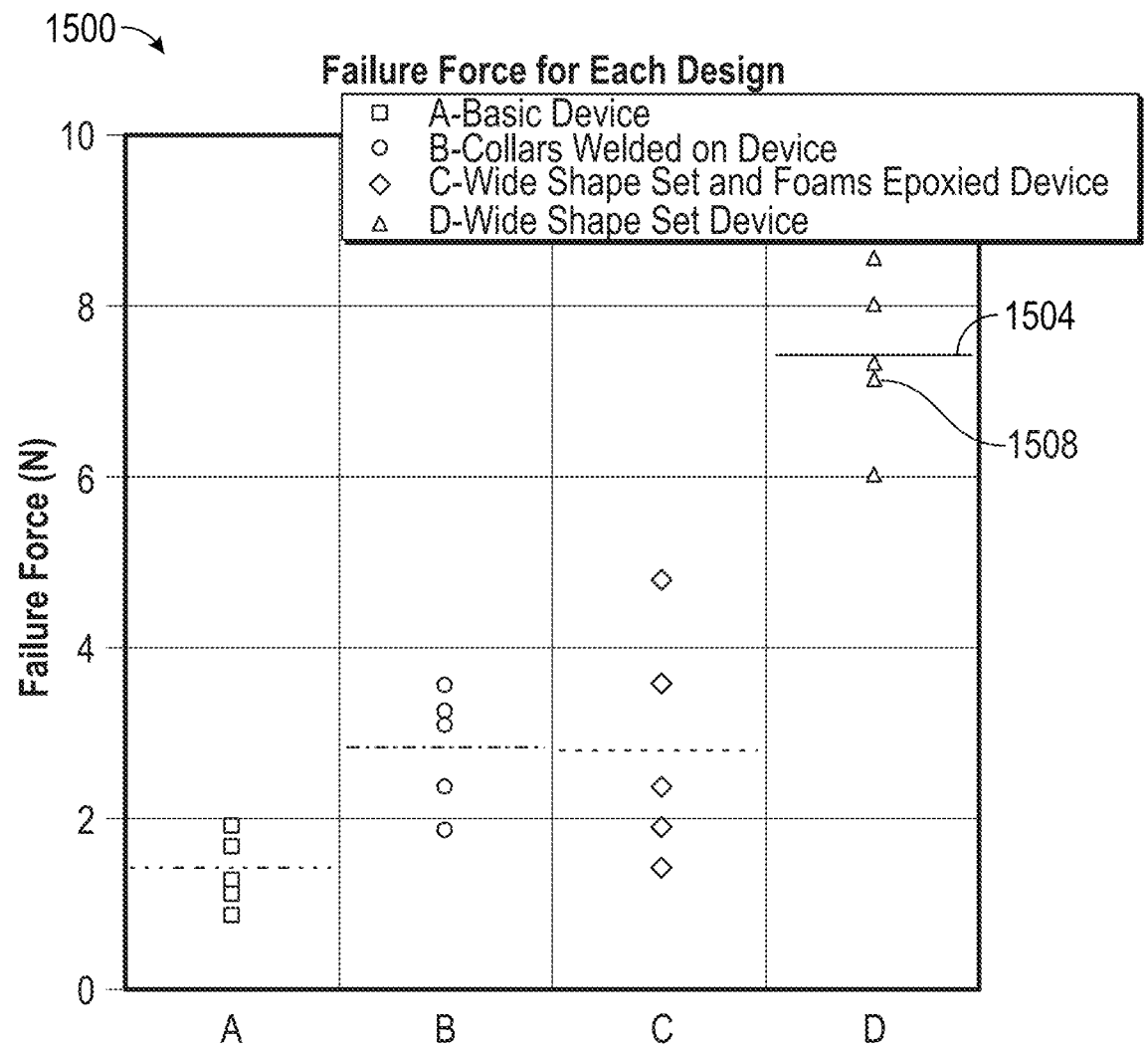
FIG. 15 depicts the maximum and average failure forces for different experimental embodiments of the embolectomy device according to embodiments of the disclosure.

FIG. 15 tabulates maximum and average forces 1500 that four different embodiments of the embolectomy device withstood. The solid lines in FIG. 15 depict an average of five experimental trials conducted for each of the four experimental embodiments of the embolectomy device, and the points in FIG. 15 depict the maximum force that each such experimental embodiment of the embolectomy device withstood. For instance, the line 1504 illustrates the average of five trials that a first experimental embodiment of the embolectomy device withstood, while the point 1508 depicts the maximum force that a first experimental embodiment of the embolectomy device withstood.

The following examples pertain to further embodiments.

Example 1 includes an embolectomy device comprised of: a guidewire; at least one expansion unit, configured to expand in diameter when actuated; and at least one support unit, configured to exert a force on the expansion unit; wherein: the at least one expansion unit is affixed to the guidewire, the at least one support unit is affixed to the guidewire, and the at least one expansion unit is situated proximately to the at least one support unit.

Example 2 includes the embolectomy device of example one, wherein the at least one expansion unit is comprised of a SMP foam, the SMP foam capable of expanding in diameter when actuated.

Example 3 includes the embolectomy device of example two, wherein the at least one expansion unit comprised of the SMP foam can be actuated by any one of heat, exposure to a solvent, laser irradiation, and resistive heating.

Example 4 includes the embolectomy device of example one, wherein the at least one support unit is comprised of any one of a SM alloy; a SMP; and an elastic material, the elastic material capable of recovering from deformations.

Example 5 includes the embolectomy device of example four, wherein the at least one support unit comprised of the SM alloy is comprised of any one of nitinol, stainless steel, and a platinum alloy.

Example 6 includes the embolectomy device of example four, wherein the at least one support unit comprised of the elastic material is comprised of any of one of platinum and SMPs.

Example 7 includes the embolectomy device of example one, wherein the guidewire is comprised of any one of nitinol, stainless steel, platinum, platinum alloy, and any other material capable of withstanding strain.

Example 8 includes the embolectomy device of example one, wherein the at least one support unit exerts an axial force on the at least one expansion unit, causing the at least one expansion unit to further expand outward radially due to exertion of the axial force.

Example 9 includes the embolectomy device of example 8, wherein the at least one support unit exerts an axial force on the at least one expansion unit after actuation of the at least one expansion unit.

Example 10 includes the embolectomy device of example one, wherein the at least one support unit includes a plurality of struts, the struts capable of expanding radially outward from the guidewire.

Example 11 includes the embolectomy device of example ten, wherein the plurality of struts of the at least one support unit are fashioned to be straight.

Example 12 includes the embolectomy device of example ten, wherein the plurality of struts of the at least one support unit are fashioned to form an 'S' shape.

Example 13 includes the embolectomy device of example one, wherein the at least one support unit is affixed to the guidewire through welding.

Example 14 includes the embolectomy device of example one, wherein the at least one expansion unit is affixed to the guidewire by crimping the expansion unit onto the guidewire.

Example 15 includes the method for removing an embolus using the embolectomy device of example one, comprising: advancing the embolectomy device of example one through a blood vessel and past an embolus within the blood vessel; actuating the at least one expansion unit of the embolectomy device of example one; retracting the embolectomy device of example one from a site of the embolus, causing the embolus to be dragged with the embolectomy device of example one.

Example 16 includes the method of example 15, wherein retracting the embolectomy device of example one from the site of the embolus further comprises: dragging the embolectomy device of example one and the embolus to a location of a sheath introduced within the blood vessel; capturing the embolus within the sheath; and removing the sheath containing the embolus.

Example 17 includes the method of example 15, wherein advancing the embolectomy device of example one through the blood vessel further comprises affixing the embolectomy device of example one onto a catheter and advancing the catheter together with the embolectomy device through the blood vessel and past the embolus.

Example 18 includes the method for fabricating the embolectomy device of example one comprising: cutting a plurality of slits into a segment of an elastic material; constraining the elastic material containing the plurality of slits to a defined shape to form the at least one support unit of the embolectomy device of example one; heating the support unit; cooling the support unit; affixing the support unit to a guidewire; cutting from a homogenous mass of SMP foam the at least one expansion unit of the embolectomy device of example one; and affixing the expansion unit to the guidewire.

Example 19 includes the method of example 18, wherein constraining the elastic material containing the plurality of slits to a defined shape to form the support unit of the embolectomy device of example one further comprises constraining the elastic material containing the plurality of slits to a shape designed to support the expansion unit.

Example 20 includes the method of example 19, wherein constraining the elastic material containing the plurality of slits to a shape designed to support the expansion unit further comprises constraining the elastic material containing the plurality of slits to a shape capable of exerting an axial force on the expansion unit.

Example 21 includes the method of example 18, wherein cutting a plurality of slits into a segment of an elastic material further comprises deburring the elastic material.

Example 22 includes the method for fabricating the embolectomy device of example one, the method comprising: forming a thermoplastic polymer elastic material into a specific shape designed to support the at least one expansion unit of the embolectomy device of example one; crosslinking the thermoplastic polymer material to form the support unit of the embolectomy device of example one; affixing the support unit to a guidewire; compressing the support unit to a diameter less than the inner diameter of a delivery catheter; cutting from a homogenous mass of SMP foam the at least one expansion unit of the embolectomy device of example one; and affixing the expansion unit to the guidewire.

Example 23 includes the method for fabricating the embolectomy device of example one, the method comprising: any one of machining a thermoset polymeric elastic material and casting reactive monomers to a thermoset polymer elastic material in a mold to form the support unit of the embolectomy device of example one; affixing the support unit to a guidewire; compressing the support unit to a diameter less than the inner diameter of a delivery catheter; cutting from a homogenous mass of SMP foam the expansion unit of the thrombectomy device of example one; affixing the expansion unit to the guidewire.

Example 24 includes the method of examples 18 through 23, wherein fabricating the embolectomy device of example one further comprises cleaning the expansion unit.

Example 25 includes the embolectomy device comprised of: at least one expansion unit, configured to expand in diameter when actuated; at least one support unit, configured to exert a force on the expansion unit; wherein: the at least expansion unit is situated proximately to the at least one support unit, and each of the at least one expansion unit and the at least one support unit is affixed to a substrate.

Example 26 includes the embolectomy device of example 25, wherein the at least one expansion unit is comprised of a SMP foam capable of expanding in diameter when actuated.

Example 27 includes the embolectomy device of example 26, wherein the at least one expansion unit comprised of the SMP foam is actuated through any one of heat, exposure to a solvent, laser irradiation, and resistive heating.

Example 28 includes the embolectomy device of example 25, wherein the at least one support unit is comprised of any one of a SM alloy; a SMP; and an elastic material, the elastic material capable of recovering from deformations.

Example 29 includes the embolectomy device of example 28, wherein the at least one support unit comprised of a SM alloy is comprised of any of nitinol, stainless steel, and a platinum alloy.

Example 30 includes the embolectomy device of example 28, wherein the at least one support unit comprised of an elastic material is comprised of any one of platinum and SMPs.

Example 31 includes the embolectomy device of claim 25, wherein the substrate is a guidewire.

Example 32 includes the embolectomy device of example 31, wherein the guidewire is comprised of any one of nitinol, stainless steel, platinum, platinum alloy, and any other material capable of withstanding strain.

Example 33 includes the embolectomy device of example 25, wherein the at least one support unit exerts an axial force on the at least one expansion unit, causing the at least one expansion unit to further expand outward radially due to the exertion of the axial force.

Example 34 includes the embolectomy device of example 33, wherein the at least one support unit exerts an axial force on the at least one expansion unit after actuation of the at least one expansion unit.

Example 35 includes the embolectomy device of example 25, wherein the at least one support unit includes a plurality of struts, the struts capable of expanding radially outward from the substrate.

Example 36 includes the embolectomy device of example 35, wherein the plurality of struts of the at least one support unit are fashioned to be straight.

Example 37 includes the embolectomy device of example 35, wherein the plurality of struts of the at least one support unit are fashioned to form an 'S' shape.

Example 38 includes the embolectomy device of example 25, wherein the at least one support unit is affixed to the substrate through welding.

Example 39 includes the embolectomy device of example 25, wherein the at least one expansion unit is affixed to the substrate by crimping the expansion unit onto the substrate.

Example 40 includes the method for removing an embolus using the embolectomy device of example 25, comprising: advancing the embolectomy device of example 25 through a blood vessel and past an embolus within the blood vessel; actuating the at least one expansion unit of the embolectomy device of example 25; retracting the embolectomy device of example 25 from a site of the embolus, causing the embolus to be dragged with the embolectomy device of example 25.

Example 41 includes the method of example 40, wherein retracting the embolectomy device of example 25 from the site of the embolus further comprises: dragging the embolectomy device of example 25 and the embolus to a location of a sheath introduced within the blood vessel; capturing the embolus within the sheath; and removing the sheath containing the embolus.

Example 42 includes the method of example 40, wherein advancing the embolectomy device of example 25 through the blood vessel further comprises affixing the embolectomy device of example 25 onto a catheter and advancing the catheter together with the embolectomy device through the blood vessel and past the embolus.

Example 43 includes the method for fabricating the embolectomy device of example 25 comprising: cutting a plurality of slits into a segment of an elastic material; constraining the elastic material containing the plurality of slits to a defined shape to form the at least one support unit of the embolectomy device of example 25; heating the support unit; cooling the support unit; affixing the support unit to the substrate of the embolectomy device of example 25; cutting from a homogenous mass of SMP foam the at least one expansion unit of the embolectomy device of example 25; and affixing the expansion unit to the substrate of the embolectomy device of example 25.

Example 44 includes the method of example 43, wherein constraining the elastic material containing the plurality of slits to a defined shape to form the support unit of the embolectomy device of example 25 further comprises constraining the elastic material containing the plurality of slits to a shape designed to exert an axial force on the at least one expansion unit of the embolectomy device of example 25.

Example 45 includes the method of example 43, wherein cutting a plurality of slits into a segment of an elastic material further comprises deburring the elastic material.

Example 46 includes the method for fabricating the embolectomy device of example 25, the method comprising: forming a thermoplastic polymer elastic material into a specific shape designed to support the at least one expansion unit of the embolectomy device of example 25; crosslinking the thermoplastic polymer material to form the support unit of the embolectomy device of example 25; affixing the support unit to a substrate of the embolectomy device of example 25; compressing the support unit to a diameter less than the inner diameter of a delivery catheter; cutting from a homogenous mass of SMP foam the at least one expansion unit of the embolectomy device of example 25; and affixing the expansion unit to the substrate of the embolectomy device of example 25.

Example 1a includes an apparatus comprising: a pusher rod having proximal and distal ends; a shape memory polymer (SMP) foam slidably coupled to the pusher rod and adjacent the distal end of the pusher rod; and a shape memory (SM) metal coupled to the pusher rod distal to the SMP foam; wherein (a)(i) a distal portion of the SM metal is permanently affixed to the pusher rod at a distal location and a proximal portion of the SM metal is slideably coupled to the pusher rod at a proximal location that is proximal to the distal location; (a)(ii) in a non-expanded configuration the SM metal and the SMP foam each have first maximum diameters orthogonal to the pusher rod; and (a)(iii) in an expanded configuration the SM metal and the SMP foam each have second maximum diameters orthogonal to the pusher rod and greater than the respective first maximum diameters.

Example 2a includes the apparatus of example 1a, wherein (b)(i) in the non-expanded configuration the SM metal and the SMP foam each have first maximum lengths parallel to the pusher rod; (b)(ii) in the expanded configuration the SM metal and the SMP foam each have second maximum lengths parallel to the pusher rod; (b)(iii) the first maximum length of the SMP foam is shorter than the second maximum length of the SMP foam and the first maximum length of the SM metal is longer than the second maximum length of the SM metal.

Example 3a includes the apparatus of example 2a, wherein in the expanded configuration the proximal portion of the SM metal forces the SMP foam (c)(i) axially parallel to the pusher rod, and (c)(ii) radially orthogonal to the pusher rod and away from the pusher rod.

Example 4a includes the apparatus of example 2a, wherein (c)(i) the first maximum length of the SMP foam is shorter than the second maximum length of the SMP foam by a SMP foam differential distance and the first maximum length of the SM metal is longer than the second maximum length of the SM metal by a SM metal differential distance; and (c)(ii) the SMP foam differential distance is greater than the SM metal differential distance.

Example 5a includes the apparatus of example 2a, wherein SM metal comprises at least two struts that couple the distal portion of the SM metal to the proximal portion of the SM metal.

Example 6a includes the apparatus of example 5a comprising a conduit coupled to proximal portions of the at least two struts, wherein the conduit is slideably coupled to the pusher rod.

Example 7a includes the apparatus of example 6a wherein the conduit slides distally along the pusher rod when the SM metal transitions from the non-expanded configuration to the expanded configuration.

Example 8a includes the apparatus of example 7a, wherein the conduit and the at least two struts are all monolithic with each other.

Example 9a includes the apparatus of example 6a comprising an additional conduit coupled to distal portions of the at least two struts.

Example 10a includes the apparatus of example 5a wherein the at least two struts directly contact a distal face of the SMP foam in the expanded configuration.

Example 11a includes the apparatus of example 10a wherein the at least two struts are substantially linear in the non-expanded configuration and substantially arcuate in the expanded configuration.

Example 12a includes the apparatus of example 10a wherein the at least two struts do not contact the distal face of the SMP foam in the non-expanded configuration.

Example 13a includes the apparatus of example 2a wherein the pusher rod passes through the SMP foam and at least a portion of the SM metal when the SMP foam and the SM metal are each in the non-expanded configuration.

Example 14a includes the apparatus of example 13a, wherein a first portion of the pusher rod is proximal to the SMP foam, a second portion of the pusher rod passes through the SMP foam when the SMP foam is in the non-expanded configuration, and a third portion of the pusher rod passes through the portion of the SM metal when the SM metal is in the non-expanded configuration.

Example 15a includes the apparatus of example 14a, wherein the first, second, and third portions of the pusher rod are monolithic with each other.

Example 16a includes the apparatus of example 2a, wherein the SMP foam transitions from the unexpanded configuration to the expanded configuration in response to thermal stimulus.

Example 17a includes the apparatus of example 2a, wherein the SMP foam includes a channel that includes a portion of the pusher rod and by which the SMP foam is slideably coupled to the pusher rod.

Example 18a includes the apparatus of example 2a comprising an endovascular catheter, wherein the pusher rod, the SMP foam, and the SM metal are all configured to simultaneously fit within the catheter.

Example 19a includes the apparatus of example 18a, wherein the catheter has a maximum outer diameter and the second maximum diameter of the SMP foam in the expanded configuration is at least 150% of the maximum outer diameter of the catheter.

Example 20a includes the apparatus of example 2a, wherein in the expanded configuration the second maximum diameter of the SM metal is less than the second maximum diameter of the SMP foam.

Example 21a includes the apparatus of example 2a, wherein in the expanded configuration the SM metal compresses the SMP foam axially and expands the SMP foam radially.

Example 22a includes the apparatus of example 21a, wherein the pusher rod includes an additional SM metal.

Example 23a includes the apparatus of example 2a, wherein the SMP foam and the SM metal transition to the expanded configuration non-simultaneously.

Example 1b includes a system comprising: a pusher rod having proximal and distal ends; a shape memory polymer (SMP) foam slidably coupled to the pusher rod and adjacent the distal end of the pusher rod; and a shape memory (SM) metal coupled to the pusher rod distal to the SMP foam; wherein the pusher rod, the SMP foam, and the SM metal are coupled to each other such that: (a)(i) a distal portion of the SM metal is statically coupled to the pusher rod and a proximal portion of the SM metal is slideably coupled to the pusher rod; (a)(ii) in a non-expanded configuration the SM metal and the SMP foam each have first maximum diameters orthogonal to the pusher rod; and (a)(iii) in an expanded configuration the SM metal and the SMP foam each have second maximum diameters orthogonal to the pusher rod and greater than the respective first maximum diameters.

A "pusher rod" constitutes a medium for advancing the system. The rod may constitute a mere wire or guide wire, such as wire 104 of FIG. 1. The rod may be monolithic and extend proximal to foam 108, through foam 108, through SM metal 112, and distal to metal 112. However, it may be non-monolithic and be composed of pieces coupled together via welding, epoxies, adhesives and the like. The guide wire may run through SM metal 112 or may stop proximal to the SM metal in varying embodiments.

In an embodiment collar 408A (FIG. 4A) is statically coupled to rod 434A while collar 404A is dynamically coupled to rod 434A and may move towards 408A when 412A contracts axially and expands radially (i.e., when transitioning from non-expanded configuration (e.g., FIG. 4A) to expanded configuration (e.g., FIG. 4B)). In an embodiment, the pusher rod may couple to a proximal portion of a SM material (e.g., SM metal or SMP) and the distal portion of the SM material may not directly coupled to the pusher rod but may be free to expand and contract to change the radial diameter of the SM material to provide support for a SMP foam that is proximal or distal to the support member that includes the SM material. A support member such as SM metal 112 may be duplicated and be both proximal and distal to the SMP foam in some embodiments.

The SM metal expands from a first max diameter 440 to a second max diameter 441. The same is true for the SMP foam at diameters 240, 241 (FIG. 2A).

In an embodiment the SMP foam is an open cell polyurethane foam. By "slideably coupled" the foam is able to slide along the rod so it is not fixedly or statically coupled but is still coupled that goes beyond merely resting against the rod. In other embodiments the foam is statically coupled to the pusher rod. In some embodiments only a portion of the SMP foam is statically coupled to the pusher rod thereby allowing another portion to dynamically couple to the pusher rod. The dynamically coupled portion may have linear expansion and/or radial expansion.

The SM metal may include an alloy of metals and the like. The SM metal may include nitinol but may include other material combinations in other embodiments.

Example 2b includes the system of example 1b wherein (b)(i) in the non-expanded configuration the SM metal and the SMP foam each have first maximum lengths parallel to the pusher rod; (b)(ii) in the expanded configuration the SM metal and the SMP foam each have second maximum lengths parallel to the pusher rod; and (b)(iii) the first maximum length of the SM metal is longer than the second maximum length of the SM metal.

For example, SM metal moves from length 442 to length 443. In some embodiments the SMP foam may change in length however in other embodiments the length of the SMP foam may be generally constant with the expansion of the foam mainly occurring radially. As used herein, and unless context dictates otherwise, "radial" is meant to be orthogonal to a pusher wire and "axial" is meant to be parallel to the pusher wire (when the pusher wire is linear and non-arcuate).

Example 3b includes the system of example 1b wherein the SM metal contracts axially when transitioning from the non-expanded state to the expanded state.

Example 4b includes the system of example 3b wherein (b)(i) in the non-expanded configuration the proximal portion of the SM metal is located a first axial distance away from a distal face of the SMP foam; (b)(ii) in the expanded configuration the proximal portion of the SM metal is located a second axial distance away from the distal face of the SMP foam, and (b)(iii) the second axial distance is greater than the first axial distance.

For example, in FIG. 7 the first axial distance 741 may constitute the distance between foam 708 and SM metal 704 in the non-expanded state while distance 742 constitutes the distance between foam 708 and SM metal 704 in the expanded state (with the differential distance shown by element 743). In some embodiments distance 741 may be 0 mm (i.e., the foam and SM metal contact each other) and foam 708 may slide along distance 743 to contact element 704 when proximal face 750 contacts a blood clot (which provides resistance to proximal movement of the foam) due to withdrawal of rod 718042 in the proximal direction 751.

In an embodiment, foam may expand linearly to cover some or all of distance 743 with or without being forced distally by an obstacle such as a blood clot. In other words, the foam's linear expansion (in some embodiments but not all embodiments) may traverse some or all of distance 743. The force between the foam and SM metal may be heightened when the foam's proximal portion encounters resistance (e.g., blood clot). In an embodiment, due to the linear expansion of the foam (e.g., in the distal direction) the SM metal may place axial and/or non-axial force against the foam to help the foam expand and fill the blood vessel. The force may be heightened when the foam's proximal portion encounters resistance (e.g., blood clot).

Example 5b includes the system of example 4b wherein the SMP foam is configured to slide distally and traverse the second axial distance when the pusher rod is moved proximally and a proximal face of the SMP foam abuts an obstacle that resists proximal movement of the SMP foam.

Such an "obstacle" may include, for example, a blood clot or other element (e.g., another SMP foam previously implanted, another medical device previously implanted).

Example 6b includes the system of example 5b wherein when the pusher rod is moved proximally and a proximal face of the SMP foam abuts an obstacle the proximal portion of the SM metal both compresses the SMP foam axially parallel to the pusher rod, and expands the SMP foam radially orthogonal to the pusher rod and away from the pusher rod.

An embodiment may include a flower like nitinol support piece that is designed to compress the foam axially and expand the foam radially when retracted. Doing so fills the breadth of the vessel and prevents fragments of the blood clot from traveling past the device.

Another version of Example 6b includes the system of example 5b wherein when the pusher rod is moved proximally and the proximal face of the SMP foam abuts the obstacle the proximal portion of the SM metal supplies both axial force against the SMP foam and non-orthogonal non-axial force against the SMP foam.

For example, when foam 312c contacts strut 316c a force will be put upon foam 312c. The force may be directed in direction 352, which has both axial components and orthogonal components. Thus, the "non-orthogonal non-axial force" may be projected along vector 352. This is important in that it forces foam 312c against vessel walls (due to the non-axial component) to help prevent downstream debris (and does so in a gentle manner that does not overly damage foam 312c). Further, the SM metal may have purely axial forces 351 in addition to the non-axial force 352. The non-axial force along direction 352 may help expand a SMP foam that is slow to expand or is otherwise having difficulty expanding due to any number of reasons (e.g., insufficient actuator stimulus, relatively weak expansion force inherent to the foam).

Example 7b includes the system of example 3b, wherein the SM metal comprises at least two struts that couple the distal portion of the SM metal to the proximal portion of the SM metal.

Example 8b includes the system of example 7b comprising a conduit coupled to proximal portions of the at least two struts, wherein the conduit is slideably coupled to the pusher rod.

For example, collar 404a constitutes such a conduit. A conduit need not be a pipe but may instead be a mere channel for conveying a substrate such as rod 434a.

Example 9b includes the system of example 8b wherein the conduit slides distally along the pusher rod when the SM metal transitions from the non-expanded configuration to the expanded configuration.

Example 10b includes the system of example 8b, wherein the conduit and the at least two struts are all monolithic with each other.

For example, see element 808 of FIG. 8.

Example 11b includes the system of example 8b comprising an additional conduit coupled to distal portions of the at least two struts.

For example, see element 408A of FIG. 4A.

Example 12b includes the system of example 7b wherein the at least two struts directly contact a distal face of the SMP foam when the pusher rod is moved proximally and a proximal face of the SMP foam abuts an obstacle that resists proximal movement of the SMP foam.

See, for example, FIG. 3C.

Example 13b includes the system of example 12b wherein the at least two struts are substantially linear in the non-expanded configuration and substantially arcuate in the expanded configuration.

Example 14b includes the system of example 12b wherein the at least two struts do not contact the distal face of the SMP foam in the non-expanded configuration.

Example 15b includes the system of example 3b wherein the pusher rod passes through the SMP foam and at least a portion of the SM metal when the SMP foam and the SM metal are each in the non-expanded configuration.

For example, see element 104 of FIG. 1.

Example 16b includes the system of example 15b, wherein a first portion of the pusher rod is proximal to the SMP foam, a second portion of the pusher rod passes through the SMP foam when the SMP foam is in the non-expanded configuration, and a third portion of the pusher rod passes through the portion of the SM metal when the SM metal is in the non-expanded configuration.

For example, see element 104 of FIG. 1.

Example 17b includes the system of example 16b, wherein the first, second, and third portions of the pusher rod are monolithic with each other.

For example, see element 808 of FIG. 8.

Example 18b includes the system of example 3b, wherein the SMP foam transitions from the unexpanded configuration to the expanded configuration in response to thermal stimulus.

Such a thermal stimulus may be due to body temperature, bodily fluids, blood, optical energy, resistive heating, a solution (e.g., saline) administered to the device, and the like. The stimulus may take place in conjunction with other actions such as plasticization and the like.

Example 19b includes the system of example 3b, wherein the SMP foam includes a channel that includes a portion of the pusher rod and by which the SMP foam is slidably coupled to the pusher rod.

Example 20b includes the system of example 3b comprising a sheath, wherein the pusher rod, the SMP foam, and the SM metal are all configured to simultaneously fit within the sheath.

Example 21b includes the system of example 20b, wherein the sheath has a maximum outer diameter and the second maximum diameter of the SMP foam in the expanded configuration is at least 150% of the maximum outer diameter of the sheath.

Other embodiments are not so limited and may include 110%, 130%, 170%, 190% or more.

Example 22b includes the system of example 3b, wherein in the expanded configuration the second maximum diameter of the SM metal is less than the second maximum diameter of the SMP foam.

Such a situation may be desirable in some embodiments where the SM metal is not meant to expand to a point where it contacts vessel walls but where the SMP foam should necessarily contact the vessel walls.

Example 23b includes the system of example 3b, wherein the pusher rod includes an additional SM metal.

Example 24b includes the system of example 3b, wherein the SMP foam and the SM metal transition to the expanded configuration non-simultaneously.

For example, the SM metal may transition as soon as it is deployed from the sheath (sometimes referred to as a catheter) while the foam may deploy from the sheath but not transition until it is warmed by blood, saline, resistive heating, and the like.

Example 25b includes a system comprising: a sheath and a pusher rod; a shape memory polymer (SMP) foam slidably coupled to the pusher rod; and a shape memory (SM) metal coupled to the pusher rod distal to the SMP foam; wherein the pusher rod, the SMP foam, and the SM metal are coupled to each other such that: (a) in a first state the pusher rod, the SMP foam, and the SM metal are included in the sheath; (b) in a second state the pusher rod, the SMP foam, and the SM metal are deployed from the sheath and, in response to being deployed from the sheath, the SM metal contracts axially, expands radially, and a proximal-most edge of the SM metal moves away from the SMP foam, (c) in a third state the SMP foam expands radially in response to being deployed from the sheath, and (d) in a fourth state the radially expanded SMP foam slides distally along the pusher rod until a distal face of the SMP foam contacts the radially expanded SM metal.

For instance, in the third state the SMP foam expands radially in response to being deployed from the sheath and may expand in response to other actions as well (e.g., exposure to thermal stimulus).

Example 26b includes the system of example 25b, wherein in the fourth state the SM metal compresses the SMP foam axially and expands the SMP foam radially.

Another version of example 26b includes the system of example 25b, wherein in the fourth state the SM metal supplies both axial force against the SMP foam and non-orthogonal, non-axial force against the SMP foam.

Example 27b includes the system of example 26b, wherein: the SM metal comprises a conduit and at least two struts; the conduit is coupled to proximal portions of the at least two struts; and the conduit is slideably coupled to the pusher rod.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. The embodiments of a device or article described herein can be manufactured, used, or shipped in a number of positions and orientations (thereby affecting "distal" vs "proximal" and the like. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A system comprising:
   a sheath and a substrate;
   a shape memory polymer (SMP) foam, wherein at least a portion of the SMP foam is slidably coupled to the substrate; and
   a multi-splined support coupled to the substrate distal to the SMP foam, wherein the multi-splined support includes at least one of a shape memory (SM) material, an elastic material, or combinations thereof;
   wherein the substrate, the SMP foam, and the multi-splined support are coupled to each other and configured such that: (a) in a first orientation the substrate, the SMP foam, and the multi-splined support are included in the sheath; (b) in a second orientation the substrate, the SMP foam, and the multi-splined support are deployed from the sheath and, in response to being deployed from the sheath, the multi-splined support contracts axially and expands radially, (c) in a third orientation the SMP foam expands radially in response to being deployed from the sheath and further in response to plasticization, and (d) in a fourth orientation the at least a portion of the radially expanded SMP foam slides distally along the substrate and towards the multi-splined support;

wherein: (a) the multi-splined support comprises at least two splines; and (b) the substrate, the SMP foam, and the at least two splines are coupled to each other and configured such that in the fourth orientation the at least two splines directly contact a distal face of the SMP foam when the substrate is moved proximally and a proximal face of the SMP foam abuts an obstacle that resists proximal movement of the SMP foam.

2. The system of claim 1, wherein the multi-splined support includes the SM material.

3. The system of claim 1, wherein in the third orientation the SMP foam expands radially in response to being deployed from the sheath and further in response to solvent-based plasticization.

4. The system of claim 1, wherein the substrate includes a pusher rod.

5. The system of claim 1, wherein:
the multi-splined support comprises a conduit;
the conduit is coupled to proximal portions of the at least two splines; and
the conduit is slidably coupled to the substrate.

6. The system of claim 5, wherein the conduit and the at least two splines are all monolithic with each other.

7. The system of claim 5, wherein the conduit is configured to slide distally along the substrate when the multi-splined support contracts axially.

8. The system of claim 5, wherein the at least two splines are substantially linear in the first orientation and substantially arcuate in the second orientation.

9. The system of claim 1, wherein in the third orientation the SMP foam contracts axially in response to being deployed from the sheath and further in response to plasticization.

10. The system of claim 1, wherein the substrate passes through the SMP foam and is included in at least a portion of the multi-splined support.

11. A system comprising:
a sheath and a substrate;
a shape memory polymer (SMP) foam, wherein at least a portion of the SMP foam is slidably coupled to the substrate; and
a multi-splined support coupled to the substrate distal to the SMP foam, wherein the multi-splined support includes at least one of a shape memory (SM) material, an elastic material, or combinations thereof;

wherein the substrate, the SMP foam, and the multi-splined support are coupled to each other and configured such that: (a) in a first orientation the substrate, the SMP foam, and the multi-splined support are included in the sheath; (b) in a second orientation the substrate, the SMP foam, and the multi-splined support are deployed from the sheath and, in response to being deployed from the sheath, the multi-splined support contracts axially and expands radially, (c) in a third orientation the SMP foam expands radially in response to being deployed from the sheath and further in response to plasticization, and (d) in a fourth orientation the at least a portion of the radially expanded SMP foam slides distally along the substrate and towards the multi-splined support;

wherein in the fourth orientation the multi-splined support directly contacts the SMP foam.

12. The system of claim 11, wherein the multi-splined support includes the SM material.

13. The system of claim 11, wherein in the third orientation the SMP foam expands radially in response to being deployed from the sheath and further in response to solvent-based plasticization.

14. The system of claim 11, wherein the substrate includes a pusher rod.

15. The system of claim 11, wherein:
the multi-splined support comprises a conduit and at least two splines;
the conduit is coupled to proximal portions of the at least two splines; and
the conduit is slidably coupled to the substrate.

16. The system of claim 15, wherein the conduit and the at least two splines are all monolithic with each other.

17. The system of claim 15, wherein the conduit is configured to slide distally along the substrate when the multi-splined support contracts axially.

18. The system of claim 15, wherein the at least two splines are substantially linear in the first orientation and substantially arcuate in the second orientation.

19. The system of claim 11, wherein in the third orientation the SMP foam contracts axially in response to being deployed from the sheath and further in response to plasticization.

20. The system of claim 11, wherein the substrate passes through the SMP foam and is included in at least a portion of the multi-splined support.

\* \* \* \* \*